US009528120B2

(12) United States Patent
Yin et al.

(10) Patent No.: US 9,528,120 B2
(45) Date of Patent: Dec. 27, 2016

(54) ARTIFICIAL PLANT PROMOTER ACTIVATED BY BROAD SPECTRUM OF XANTHOMONAS

(71) Applicant: TEMASEK LIFE SCIENCES LABORATORY LIMITED, Singapore (SG)

(72) Inventors: Zhongchao Yin, Singapore (SG); Xuan Zeng, Singapore (SG); Dongsheng Tian, Singapore (SG)

(73) Assignee: TEMASEK LIFE SCIENCES LABORATORY LIMITED, Singapore (SG)

( * ) Notice: Subject to any disclaimer, the term of this patent is extended or adjusted under 35 U.S.C. 154(b) by 54 days.

(21) Appl. No.: 14/439,968

(22) PCT Filed: Nov. 1, 2012

(86) PCT No.: PCT/SG2012/000414
§ 371 (c)(1),
(2) Date: Apr. 30, 2015

(87) PCT Pub. No.: WO2014/070102
PCT Pub. Date: May 8, 2014

(65) Prior Publication Data
US 2015/0291974 A1 Oct. 15, 2015

(51) Int. Cl.
*C07H 21/04* (2006.01)
*C12N 15/82* (2006.01)
*C25D 11/02* (2006.01)
*C25D 11/34* (2006.01)
*C07K 14/00* (2006.01)
*F16L 58/00* (2006.01)

(52) U.S. Cl.
CPC ......... *C12N 15/8281* (2013.01); *C07K 14/001* (2013.01); *C12N 15/8239* (2013.01); *C25D 11/024* (2013.01); *C25D 11/34* (2013.01); *C23F 2213/21* (2013.01); *C23F 2213/31* (2013.01); *F16L 58/00* (2013.01)

(58) Field of Classification Search
None
See application file for complete search history.

(56) References Cited

FOREIGN PATENT DOCUMENTS

WO 2012033462 A1 3/2012

OTHER PUBLICATIONS

Zeng et al. Genetic engineering of the Xa10 promoter for broad-spectrum and durable resistance to Xanthomonas oryzae pv. oryzae. (2015) Plant Biotechnology Journal; vol. 13; pp. 993-1001.*
International Search Report mailed Dec. 3, 2012, , Application No. PCT/SG2012/000414, filing Date: Nov. 1, 2012, Temasek Life Sciences Laboratory Limited, 5 pages.

* cited by examiner

*Primary Examiner* — Cathy Kingdon Worley
(74) *Attorney, Agent, or Firm* — Rothwell, Figg, Ernst & Manbeck, P.C.

(57) ABSTRACT

The present invention relates to synthetic promoter and a synthetic gene which confers broad-spectrum disease resistance to Xanthomonands in plants. The present invention also relates to transgenic plants containing the synthetic gene and plants derived by crossing plants with such transgenic plants. More specifically, the synthetic promoter is a synthetic Xa10 promoter and the synthetic gene is a synthetic Xa10 gene which contains the synthetic Xa10 promoter. The resistance is resistance to bacterial blight and the plants are rice plants.

23 Claims, 4 Drawing Sheets

ARTIFICIAL PLANT PROMOTER ACTIVATED BY BROAD SPECTRUM OF XANTHOMONAS

CROSS-REFERENCE TO RELATED APPLICATIONS

The present application is a national stage filing under 35 U.S.C. §371 of PCT/SG2012/000414, filed on 1 Nov. 2012, which is incorporated herein by reference in its entirety.

SEQUENCE SUBMISSION

The present application is being filed along with a Sequence Listing in electronic format. The Sequence Listing is entitled 2577227SequenceListing.txt, created on 24 Oct. 2012 and is 29 kb in size. The information in the electronic format of the Sequence Listing is incorporated herein by reference in its entirety.

BACKGROUND OF THE INVENTION

The present invention relates to synthetic promoter and a synthetic gene which confers broad-spectrum disease resistance to Xanthomonands in plants. The present invention also relates to transgenic plants containing the synthetic gene and plants derived by crossing plants with such transgenic plants. More specifically, the synthetic promoter is a synthetic Xa10 promoter and the synthetic gene is a synthetic Xa10 gene which contains the synthetic Xa10 promoter. The resistance is resistance to bacterial blight and the plants are rice plants.

The publications and other materials used herein to illuminate the background of the invention or provide additional details respecting the practice, are incorporated by reference, and for convenience are respectively grouped in the Bibliography.

Gram-negative phytopathogenic bacteria employ a type III secretion system (TTSS) to translocate effector proteins into plant cells where they modulate host cell functions for the benefit of the invasion process (Alfano and Collmer, 2004; Kay and Bonas, 2009). Members of the large AvrBs3 effector family are unique kind of type III effectors produced by pathovars of *Xanthomonas* and *Ralstonia solanacearum* (Bonas et al., 1989; Yang and White, 2004; Heuer et al., 2007). AvrBs3-like effectors, also recently referred to as transcription activator-like (TAL) effectors (Yang et al., 2006; Bogdanove et al., 2010), have in common an N-terminus required for type III secretion and a C-terminus containing nuclear localization signals (NLS) and an acidic activation domain (AAD). TAL effectors differ in the middle, a region of typically 33-35 amino acid (aa) long, near-perfect repeats that ends in a 20 aa long truncated repeat. The two hypervariable amino acids at position 12 and 13 of repeats, also termed as repeat-variable di-residue (RVD) (Moscow and Bogdanove, 2009), contribute to repeat polymorphism, whereas the number and order of repeats with polymorphic RVDs in a TAL effector determine the specific activity (Herbers et al., 1992; Yang et al., 2005).

Individual TAL effectors activate transcription of specific host susceptibility (S) genes for promoting disease development (Yang et al., 2006; Kay et al., 2007; Sugio et al., 2007; Antony et al., 2010). In order to counteract the disease-promoting strategies, plants have evolved mechanisms that exploit the transcription inducing ability of the TAL effectors (Gu et al., 2005; Romer et al., 2007). Thus, a subset of TAL effectors functions as avirulence effectors and activates the transcription of disease R genes. TAL effectors bind specific DNA sequences in the promoters of S or R genes (Kay et al., 2007; Romer et al., 2007; Romer et al., 2009; Antony et al., 2010). Each RVD from the central repeats of TAL effectors specifically recognizes a nucleotide in the target DNA element with a conserved T at the 5' end (Boch and Bonas, 2010; Bogdanove et al., 2010).

*Xanthomonas oryzae* pv. *oryzae* is the causal agent of bacterial blight of rice (Nino-Liu et al., 2006). Individual strains of *X. oryzae* pv. *oryzae* harbor 11 to 19 TAL effectors (White et al., 2009). TAL effectors from *X. oryzae* pv. *oryzae* target to rice genes for either susceptibility (Yang et al., 2006; Sugio et al., 2007; Chen et al., 2010) or resistance to bacterial infection (Gu et al., 2005). TAL effector PthXo1 from *X. oryzae* pv. *oryzae* strain $PXO99^A$ targets Os8N3/Xa13/OsSWEET11 in rice (Yang et al., 2006; Chen et al., 2010). The recessive allele of Xa13 (xa13) is unresponsive to PthXo1, and plants with xa13 are resistant to strains of the pathogen that rely solely on the PthXo1 as the essential effector for virulence (Yang et al., 2006). The xa13-mediated resistance to rice bacterial blight can be defeated by induction of the S gene Os-11N3, another member of the N3 gene family, by strains of the pathogen utilizing the TAL effectors AvrXa7 and PthXo3 (Antony et al., 2010).

PthXo6 and PthXo7 are two other TAL effectors from $PXO99^A$ and target respectively to two transcription factor genes, OsTFX1 and OsTFIIA γ1, in rice (Sugio et al., 2007). OsTFX1 encodes a bZIP transcription factor whereas the gene product of OsTFIIA γ1 is the small subunit of the transcription factor HA (Sugio et al., 2007). The induction of OsTFIIA γ1 located on chromosome 1 by PthXo7 may reflect the adaptation of $PXO99^A$ to the resistance mediated by xa5 (Iyer and McCouch, 2004), an allele of OsTFIIA γ5 encoding a second form of the TFIIA small subunit on chromosome 5 of rice (Sugio et al., 2007). The DNA target sequences of PthXo1, $EBE_{PthXo1}$ (Effector Binding Element for PthXo1), has been identified in the promoter of Os8N3 (Antony et al., 2010), whereas the DNA target sequences of PthXo6 and PthXo7 remain to be identified or verified in the promoters of OsTFX1 and OsTFIIA γ1, respectively, although the putative target sequences were predicted (Boch et al., 2009).

Three TAL effectors, AvrXa7 and AvrXal10 from PXO86 (Hopkins et al., 1992) and AvrXa27 from $PXO99^A$ (Gu et al., 2005), activate disease resistance when rice plants carried the cognate R genes Xa7, Xa10 or Xa27. So far, only the Xa27 gene has been isolated and published (Gu et al., 2005). Xa27 is induced by AvrXa27 and the gene can provide non-specific resistance to *X. oryzae* pv. *oryzae* if the AvrXa27-inducible promoter is replaced with a stress-inducible promoter from the rice PR1 gene (Gu et al., 2005; Tian and Yin, 2009). The full induction of Xa27 by AvrXa27 requires OsTFIIA γ5, the gene product of Xa5 on chromosome 5 (Gu et al., 2009). A 16- to 18-bp DNA cis-element, designated as $UPT_{AvrXa27}$ (UPregulated by TAL effector AvrXa27 or $EBE_{AvrXa27}$), was identified in the promoter of Xa27 to be specifically induced by AvrXa27 (Boch et al., 2009; Romer et al., 2009).

Xa10 confers narrow-spectrum race-specific resistance to a few Philippine races of *X. oryzae* pv. *oryzae* (Yoshimura et al., 1995). The R gene was introgressed from rice cultivar Cas 209 into susceptible rice variety IR24 (Mew, 1982; Yoshimura et al., 1983). Xa10 was finely mapped to a genetic region of 0.28 cM between proximal marker M491 and distal marker M419 on the long arm of chromosome 11 and co-segregated with markers S723 and M604 (Gu et al., 2008). The Xa10 gene was recently cloned by map-based cloning and genetic transformation approaches (International Published Application No. WO 2012/033462). A functional target sequence of AvrXa10, $EBE_{AvrXa}10$ was identified in the promoter of Xa10 (International Published Application No. WO 2012/033462). The Xa10 gene product, XA10, is functional in both monocots and dicots by inducing hypersensitive response (HR)-like cell death (unpublished).

The resistance specificity of TAL effector-dependent R gene to bacterial blight is determined by the R gene promoter rather than the R gene products (Gu et al., 2005). Meanwhile, the spectrum of TAL effector-dependent R genes to bacterial blight varies greatly, which is depended on the availability of the avirulence TAL effectors in the *X. oryzae* pv. *oryzae* strains (Gu et al., 2004; Gu et al., 2008). Romer et al (2009) demonstrated that multiple functionally distinct DNA elements targeted by separate TAL effectors retain their function and specificity when combined into one promoter. It is desired to generate broad-spectrum resistance to bacterial blight in rice.

SUMMARY OF THE INVENTION

The present invention relates to synthetic promoter and a synthetic gene which confers broad-spectrum disease resistance to Xanthomonands in plants. The present invention also relates to transgenic plants containing the synthetic gene and plants derived by crossing plants with such transgenic plants. More specifically, the synthetic promoter is a synthetic Xa10 promoter and the synthetic gene is a synthetic Xa10 gene which contains the synthetic Xa10 promoter. The resistance is resistance to bacterial blight and the plants are rice plants.

Thus, in a first aspect, the present invention provides a synthetic promoter comprising a rice Xa10 promoter that has been modified to contain multiple Effector Binding Elements (EBE) each of which binds a different transcription activator-like (TAL) effector. In one embodiment, the synthetic promoter contains an $EBE_{pthXo7}$ sequence. In another embodiment, the synthetic promoter contains an $EBE_{pthXo1}$ sequence. In an additional embodiment, the synthetic promoter contains an $EBE_{AvrXa10}$ sequence. In a further embodiment, the synthetic promoter contains an $EBE_{pthXo6}$ sequence. In another embodiment, the synthetic promoter contains an $EBE_{AvrXa27}$ sequence. In an additional embodiment, the synthetic promoter contains all five of these EBE sequences. In one embodiment, the synthetic promoter is a synthetic mini promoter that contains one to five of the EBE sequences and the minimal portion of the rice Xa10 promoter to possess promoter activity. In another embodiment, the synthetic promoter is a synthetic full length Xa10 that contains one to five of the EBE sequences. In one embodiment, the synthetic full length promoter contains the synthetic mini promoter. In a further embodiment, the synthetic promoter is any fragment of the synthetic full length promoter that is larger than the synthetic mini promoter, that is contiguous to the 5' end of the synthetic mini promoter, and that possesses promoter activity.

In one embodiment, the synthetic mini promoter comprises the sequence set forth in SEQ ID NO:2. In another embodiment, the synthetic full length promoter comprises the sequence set forth in SEQ ID NO:10. In a further embodiment, the synthetic promoter comprises nucleotides 2208-2456 and any number of nucleotides 5' to the synthetic mini promoter and contiguous to the synthetic mini promoter. In one embodiment, the $EBE_{pthXo7}$ sequence comprises the sequence set forth in SEQ ID NO:5. In another embodiment, the $EBE_{pthXo1}$ sequence comprises the sequence set forth in SEQ ID NO:6. In an additional embodiment, the $EBE_{AvrXa10}$ sequence comprises the sequence set forth in SEQ ID NO:7. In a further embodiment, the $EBE_{pthXo6}$ sequence comprises the sequence set forth in SEQ ID NO:8. In another embodiment, the $EBE_{AvrXa27}$ sequence comprises the sequence set forth in SEQ ID NO:9.

In a second aspect, the present invention provides a synthetic Xa10 gene which comprises a synthetic promoter of the present invention operably linked to a rice Xa10 sequence. In one embodiment, the start codon of the rice Xa10 sequence is contiguous to the 3' end of the synthetic promoter. In another embodiment, the rice Xa10 sequence is the coding sequence of the rice Xa10 protein. In a further embodiment, the Xa10 sequence is a genomic sequence encoding the rice Xa10 protein. In another embodiment, the rice Xa10 sequence is the coding sequence plus the '3 UTR containing the terminator. In a further embodiment, the rice Xa10 terminator (nucleotides 382-759 of SEQ ID NO:15) can be replaced by other terminators well known to the skilled artisan, such as a NOS terminator, a 35S terminator and a Xa27 terminator. In one embodiment, the coding sequence comprises the coding sequence set forth in SEQ ID NO:13. In another embodiment, a genomic sequence encoding the rice Xa10 protein comprises the sequence set forth in SEQ ID NO:15 which includes the coding sequence (nucleotides 1-381) and the terminator (nucleotides 382-759). In a further embodiment, a genomic sequence encoding the rice Xa10 protein comprises the sequence set forth in SEQ ID NO:16 which includes the coding sequence (nucleotides 1-381), the terminator (nucleotides 382-759) and further 3' UTR (nucleotides 760-1193). In another embodiment, a genomic sequence encoding the rice Xa10 protein comprises the sequence set forth in SEQ ID NO:17 which includes the coding sequence (nucleotides 1-381), the terminator (nucleotides 382-759) and further 3' UTR (nucleotides 760-2215). In another embodiment, the rice Xa10 sequence comprises the sequence set forth in nucleotides 1-759 of SEQ ID NO:17 plus any number of nucleotides 3' of the terminator in SEQ ID NO:17 that are contiguous to the terminator. In one embodiment, the sequence of a synthetic Xa10 gene is set forth in SEQ ID NO:11. In another embodiment, the sequence of a synthetic Xa10 gene is set forth in SEQ ID NO:12.

In a third aspect, the present invention provides a vector comprising a synthetic Xa10 gene described herein. The present invention also provides a plant cell comprising the vector and a transgenic plant having broad-spectrum resistance to bacterial blight comprising the plant cell. In one embodiment, the plant cell is a rice cell. In another embodiment, the transgenic plant is a transgenic rice plant.

In a fourth aspect, the present invention provides a method of making a transgenic plant having broad-spectrum resistance to bacterial blight. In accordance with the present invention, the method comprises transfecting a synthetic Xa10 gene described herein or a vector comprising a synthetic Xa10 gene described herein into a plant cell or into plant cells and producing a transgenic plant from the transfected plant cell or transfected plant cells. In accordance with the present invention, the synthetic Xa10 gene is expressed in the transgenic plant. Transfecting the synthetic Xa10 gene or vector into a plant cell or into plant cells is also sometimes referred to herein as transforming a plant cell or plant cells with the synthetic Xa10 gene or vector. In one embodiment, the plant cell or cells is a rice cell or cells.

In a fifth aspect, the present invention provides a transgenic plant having at least one copy of a synthetic Xa10 gene described herein stably incorporated into its genome. In one embodiment, the transgenic plant contains two copies of the synthetic Xa10 gene. In another embodiment, the transgenic plant contains three copies of the synthetic Xa10 gene. In an additional embodiment, the transgenic plant contains four copies of the synthetic Xa10 gene. In a further embodiment, the transgenic plant contains five copies of the synthetic Xa10 gene. In another embodiment, the transgenic plant contains six copies of the synthetic Xa10 gene. In one embodiment, the plant is a rice plant. In another embodiment, the transgenic rice plant is referred to herein as the L2 plant or L2 line. The present invention also provides for a plant that contains a synthetic Xa10 gene described herein stably incorporated into its genome that is derived by crossing a transgenic plant described herein or its progeny with a second plant and selecting progeny that contain the synthetic Xa10 gene. In accordance with the present invention, the transgenic plant or plants of the present invention can be used in conventional breeding programs. In one embodiment, the transgenic plant used in a breeding program is the transgenic rice plant referred to herein as the L2 plant or L2 line or progeny thereof.

BRIEF DESCRIPTION OF THE FIGURES

FIG. 2A: Southern blot analysis of $T_1$ plants of L2 detected with Hpt probe. FIG. 2B: Southern blot analysis of $T_2$ plants of L2 detected with Hpt probe. FIG. 2C: Southern blot analysis of $T_2$-36 and its $T_3$ progeny detected with Xa10 probe. About 2 μg of DNA samples were digested with restriction enzymes BamHI and XbaI. The phenotypes of plants were shown below the images of Southern blot analyses. Arrows indicate the bands that co-segregated with the resistant phenotype. NB, Nipponbare.

FIG. 4A: Relative expression of Xa10 in IRBB10A and L2 plants. Xa10 transcripts were determined by qRT-PCR at 24 hpi. The expression of Xa10 in IRBB10A inoculated 1947(pHM1avrXa10) was set as "1". The rice ubiquitin gene 1 (Ubi1) was used as an internal control. FIG. 4B: PCR products after amplification with real-time RT-PCR. Samples in FIGS. 4A and 4B: 1, IRBB10A plants inoculated with water (mock inoculation); 2, IRBB10A plants inoculated with 1947; 3, IRBB10A plants inoculated with 1947(pHM1avrXa10); 4, L2 plants inoculated with water (mock inoculation); 5, L2 plants inoculated with 1947; 6, L2 plants inoculated with 1947(pHM1avrXa10); 7, L2 plants inoculated with 1947(pHM1avrXa27); 8, L2 plants inoculated with 1947(pHM1pthXo1); 9, L2 plants inoculated with 1947(pHM1pthXo6); 10, L2 plants inoculated with 1947(pHM1pthXo7).

DETAILED DESCRIPTION OF THE INVENTION

Figure 1:
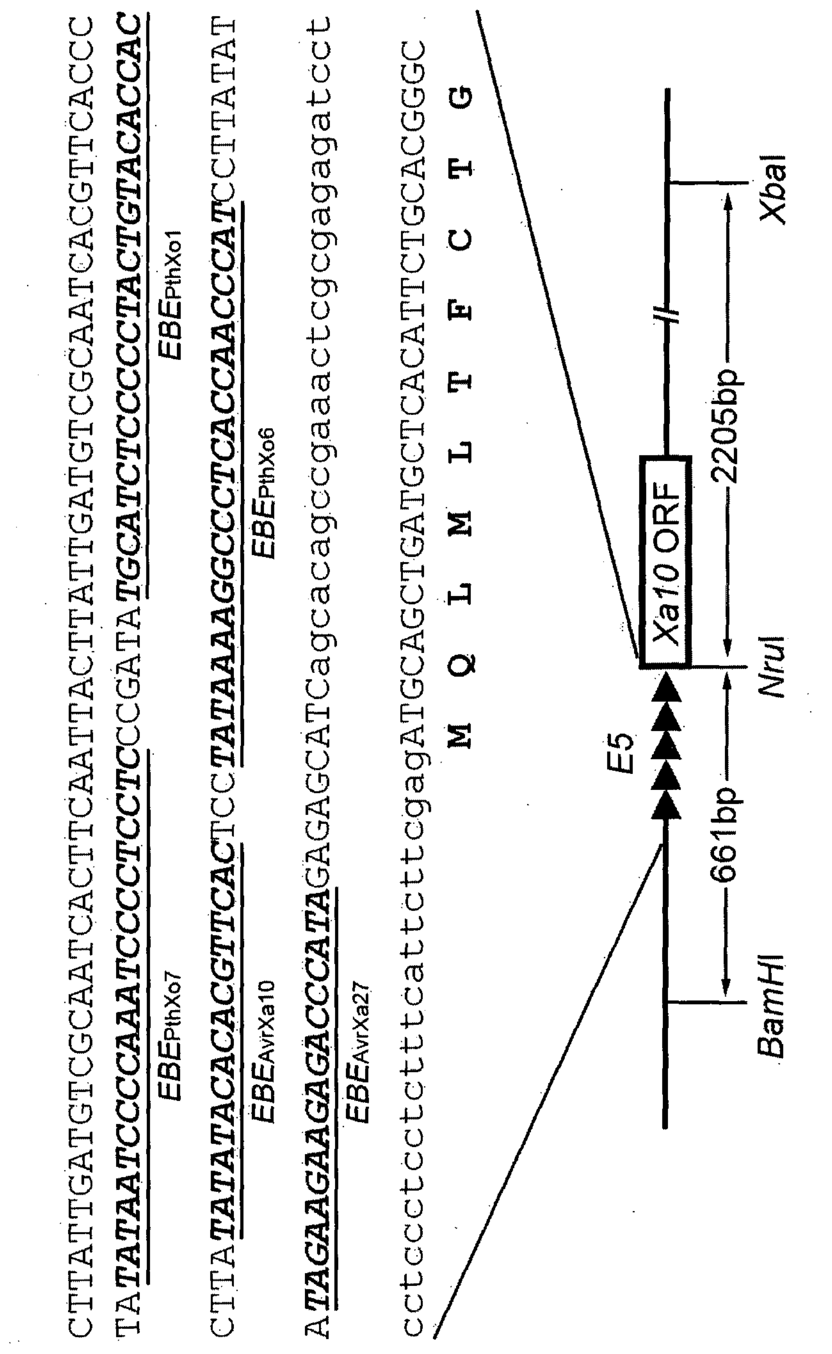
FIG. 1 shows the gene organization of $Xa10^{E5}$. The nucleotide sequences of $EBE_{pthXo7}$, $EBE_{pthXo1}$, $EBE_{AvrXa10}$, $EBE_{pthXo6}$ and $EBE_{AvrXa27}$ in the promoter of Xa10 gene are shown in bold and italic letters. The nucleotide sequences of the 5' untranslated region of $Xa10^{E5}$ are shown in lower letters. The restriction sites of BamHI, NruI and XbaI, and the size of DNA restriction fragments are indicated. Map was not drawn to scale. Xa10 ORF, open reading frame of the Xa10 gene. The sequences shown in FIG. 1 are as follow: full length sequence: SEQ ID NO:1; $Xa10^{E5}$ mini promoter (does not include Xa10 ORF): SEQ ID NO:2; Xa10 partial ORF shown: SEQ ID NO:3; Xa10 partial peptide shown: SEQ ID NO:4; $EBE_{PthXo7}$: SEQ ID NO:5; $EBE_{PthXo1}$: SEQ ID NO:6; $EBE_{AvrXa10}$: SEQ ID NO:7; $EBE_{PthXo6}$: SEQ ID NO:8; $EBE_{AvrXa27}$: SEQ ID NO:9.

The present invention relates to synthetic promoter and a synthetic gene which confers broad-spectrum disease resistance to Xanthomonands in plants. The present invention also relates to transgenic plants containing the synthetic gene and plants derived by crossing plants with such transgenic plants. More specifically, the synthetic promoter is a synthetic Xa10 promoter and the synthetic gene is a synthetic Xa10 gene which contains the synthetic Xa10 promoter. The resistance is resistance to bacterial blight and the plants are rice plants.

By "isolated" is meant a biological molecule free from at least some of the components with which it naturally occurs.

As used herein, "gene" refers to a nucleic acid sequence that encompasses a 5' promoter region associated with the expression of the gene product, any intron and exon regions and 3' or 5' untranslated regions associated with the expression of the gene product.

As used herein, "genotype" refers to the genetic constitution of a cell or organism.

As used herein, "phenotype" refers to the detectable characteristics of a cell or organism, which characteristics are the manifestation of gene expression.

The terms "polynucleotide," "nucleotide sequence," and "nucleic acid" are used to refer to a polymer of nucleotides (A, C, T, U, G, etc. or naturally occurring or artificial nucleotide analogues), e.g., DNA or RNA, or a representation thereof, e.g., a character string, etc., depending on the relevant context. A given polynucleotide or complementary polynucleotide can be determined from any specified nucleotide sequence.

A nucleic acid or polypeptide is "recombinant" when it is artificial or engineered, or derived from an artificial or engineered protein or nucleic acid. For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

The term "nucleic acid construct" or "polynucleotide construct" means a nucleic acid molecule, either single- or double-stranded, which is isolated from a naturally occurring gene or which has been modified to contain segments of nucleic acids in a manner that would not otherwise exist in nature. The term nucleic acid construct is synonymous with the term or "expression cassette" when the nucleic acid construct contains the control sequences required for expression of a sequence of the present invention. A "vector" is another type of nucleic acid construct. The vector may be an expression vector, a replication vector or a transformation vector.

The term "control sequences" is defined herein to include all components, which are necessary or advantageous for the expression of a polynucleotide of the present invention. Each control sequence may be native or foreign to the polynucleotide sequence. At a minimum, the control sequences include a promoter and transcriptional stop signals. The control sequences may be provided with linkers for the purpose of introducing specific restriction sites facilitating ligation of the control sequences to the nucleotide sequence.

The term "operably linked" is defined herein as a configuration in which a control sequence is appropriately placed at a position relative to the nucleotide sequence of the nucleic acid construct such that the control sequence directs the expression of a polynucleotide of the present invention.

In the present context, the term "expression" includes transcription of the polynucleotide. In the present context, the term "expression vector" covers a DNA molecule, linear or circular, that comprises a polynucleotide of the invention, and which is operably linked to additional segments that provide for its transcription.

"Protein modifications" are provided by the present invention which include one or more amino acid substitutions. Substitutional variants typically contain the exchange of one amino acid for another at one or more sites within the protein, and may be designed to modulate one or more properties of the polypeptide, such as stability against proteolytic cleavage, without the loss of other functions or properties. Amino acid substitutions may be made on the basis of similarity in polarity, charge, solubility, hydrophobicity, hydrophilicity, and/or the amphipathic nature of the residues involved. Preferred substitutions are ones which are conservative, that is, one amino acid is replaced with one of similar shape and charge. Conservative substitutions are well known to persons of ordinary skill in the art and typically include, though not exclusively, substitutions within the following groups: glycine, alanine; valine, isoleucine, leucine; aspartic acid, glutamic acid; asparagine, glutamine; serine, threonine; lysine, arginine; and tyrosine, phenylalanine.

Certain amino acids may be substituted for other amino acids in a protein structure without appreciable loss of interactive binding capacity with structures such as, for example, antigen-binding regions of antibodies or binding sites on substrate molecules or binding sites on proteins interacting with a polypeptide. Since it is the interactive capacity and nature of a protein which defines that protein's biological functional activity, certain amino acid substitutions can be made in a protein sequence, and its underlying DNA coding sequence, and nevertheless obtain a protein with like properties. In making such changes, the hydropathic index of amino acids may be considered. The importance of the hydrophobic amino acid index in conferring interactive biological function on a protein is generally understood in the art. Alternatively, the substitution of like amino acids can be made effectively on the basis of hydrophilicity. The importance of hydrophilicity in conferring interactive biological function of a protein is generally understood in the art (See e.g. U.S. Pat. No. 4,554,101). The use of the hydrophobic index or hydrophilicity in designing polypeptides is further discussed in U.S. Pat. No. 5,691,198.

The term "plant" includes whole plants, shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit (the mature ovary), plant tissue (e.g. vascular tissue, ground tissue, and the like) and cells (e.g. guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid and hemizygous.

The term "heterologous" as used herein describes a relationship between two or more elements which indicates that the elements are not normally found in proximity to one another in nature. Thus, for example, a polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is not naturally associated with the promoter (e.g. a genetically engineered coding sequence or an allele from a different ecotype or variety). An example of a heterologous polypeptide is a polypeptide expressed from a recombinant polynucleotide in a transgenic organism. Heterologous polynucleotides and polypeptides are forms of recombinant molecules.

The term "transfecting" as used herein refers to the deliberate introduction to a nucleic acid into a cell. Transfection includes any method known to the skilled artisan for introducing a nucleic acid into a cell, including, but not limited to, *Agrobacterium* infection, ballistics, electroporation, microinjection and the like.

The term "broad-spectrum disease resistance" as used herein refers to resistance to a wide variety of strains of a causative agent. As an example, a wide variety of strains may be strains of *Xanthomonas oryzae* pv. *oryzae* and the disease bacterial blight in rice.

TAL effectors from xanthomonads target host genes for promoting disease or triggering disease resistance. They bind to the effector binding elements (EBEs) in the promoters of host genes and induce their expression. Xa10 is an R gene in rice that confer race-specific resistance to *Xanthomonas oryzae* pv. *oryzae*, the causal agent of bacterial blight in rice. The Xa10 gene product, XA10, is functional in both monocots and dicots by inducing hypersensitive response (HR)-like cell death.

In accordance with the present invention, novel resistance specificity and increased resistance spectrum of the Xa10 genes are accomplished by synthesizing a modified Xa10 gene with an engineered promoter containing 5 EBEs targeted by either virulent or avirulent TAL effectors (termed $Xa10^{E5}$ herein). The $Xa10^{E5}$ gene was generated and used for production of transgenic rice. A stable transgenic rice line, L2, was obtained. L2 had two copies of the $Xa10^{E5}$ gene and conferred disease resistance to bacterial blight. The $Xa10^{E5}$ gene in L2 plants was specifically induced by *X. oryzae* pv. *oryzae* strains expressing one of the corresponding TAL effectors and conferred broad-spectrum resistance to 27 of the 28 field strains of *X. oryzae* pv. *oryzae* tested.

Thus, in a first aspect, the present invention provides a synthetic promoter comprising a rice Xa10 promoter that has been modified to contain multiple Effector Binding Elements (EBE) each of which binds a different transcription activator-like (TAL) effector. In one embodiment, the synthetic promoter contains an $EBE_{pthXo7}$ sequence. In another embodiment, the synthetic promoter contains an $EBE_{pthXo1}$ sequence. In an additional embodiment, the synthetic promoter contains an $EBE_{AvrXa10}$ sequence. In a further embodiment, the synthetic promoter contains an $EBE_{pthXo6}$ sequence. In another embodiment, the synthetic promoter contains an $EBE_{AvrXa27}$ sequence. In an additional embodiment, the synthetic promoter contains all five of these EBE sequences. In one embodiment, the synthetic promoter is a synthetic mini promoter that contains one to five of the EBE sequences and the minimal portion of the rice Xa10 promoter to possess promoter activity. In another embodiment, the synthetic promoter is a synthetic full length Xa10 that contains one to five of the EBE sequences. In one embodiment, the synthetic full length promoter contains the synthetic mini promoter. In a further embodiment, the synthetic promoter is any fragment of the synthetic full length promoter that is larger than the synthetic mini promoter, that is contiguous to the 5' end of the synthetic mini promoter, and that possesses promoter activity.

In one embodiment, the synthetic mini promoter comprises the sequence set forth in SEQ ID NO:2. In another embodiment, the synthetic full length promoter comprises the sequence set forth in SEQ ID NO:10. In an additional embodiment, the synthetic promoter comprises nucleotides 2208-2456 of the sequence set forth in SEQ ID NO:10 and any number of nucleotides that are contiguous and are contiguous to nucleotide 2208. In one embodiment, the synthetic promoter comprises nucleotides 2200-2456 of the sequence set forth in SEQ ID NO:10. In another embodiment, the synthetic promoter comprises nucleotides 2100-2456 of the sequence set forth in SEQ ID NO:10. In an additional embodiment, the synthetic promoter comprises nucleotides 1950-2456 of the sequence set forth in SEQ ID NO:10. In a further embodiment, the synthetic promoter comprises nucleotides 1500-2456 of the sequence set forth in SEQ ID NO:10. In another embodiment, the synthetic promoter comprises nucleotides 1225-2456 of the sequence set forth in SEQ ID NO:10. In an additional embodiment, the synthetic promoter comprises nucleotides 1099-2456 of the sequence set forth in SEQ ID NO:10. In a further embodiment, the synthetic promoter comprises nucleotides 1438-2456 of the sequence set forth in SEQ ID NO:10. In another embodiment, the synthetic promoter comprises nucleotides 987-2456 of the sequence set forth in SEQ ID NO:10. In an additional embodiment, the synthetic promoter comprises nucleotides 542-2456 of the sequence set forth in SEQ ID NO:10. In a further embodiment, the synthetic promoter comprises nucleotides 15-2456 of the sequence set forth in SEQ ID NO:10. These examples of synthetic promoters are exemplary only and illustrate that the inventors contemplate any synthetic promoter comprising 250-2456 contiguous nucleotides that must include nucleotides 2208-2246 of SEQ ID NO:10.

In one embodiment, the $EBE_{pthXo7}$ sequence comprises the sequence set forth in SEQ ID NO:5. In another embodiment, the $EBE_{pthXo1}$ sequence comprises the sequence set forth in SEQ ID NO:6. In an additional embodiment, the $EBE_{AvrXa10}$ sequence comprises the sequence set forth in SEQ ID NO:7. In a further embodiment, the $EBE_{pthXo6}$ sequence comprises the sequence set forth in SEQ ID NO:8. In another embodiment, the $EBE_{AvrXa27}$ sequence comprises the sequence set forth in SEQ ID NO:9.

In a second aspect, the present invention provides a synthetic Xa10 gene which comprises a synthetic promoter of the present invention operably linked to a rice Xa10 sequence. In one embodiment, the start codon of the rice Xa10 sequence is contiguous to the 3' end of the synthetic promoter. In another embodiment, the rice Xa10 sequence is the coding sequence of the rice Xa10 protein. In a further embodiment, the Xa10 sequence is a genomic sequence encoding the rice Xa10 protein. In another embodiment, the rice Xa10 sequence is the coding sequence plus the '3 UTR containing the terminator. In a further embodiment, the rice Xa10 terminator (nucleotides 382-759 of SEQ ID NO:15) can be replaced by other terminators well known to the skilled artisan, such as a NOS terminator, a 35S terminator and a Xa27 terminator. In one embodiment, the coding sequence comprises the coding sequence set forth in SEQ ID NO:13. In another embodiment, a genomic sequence encoding the rice Xa10 protein comprises the sequence set forth in SEQ ID NO:15 which includes the coding sequence (nucleotides 1-381) and the terminator (nucleotides 382-759). In a further embodiment, a genomic sequence encoding the rice Xa10 protein comprises the sequence set forth in SEQ ID NO:16 which includes the coding sequence (nucleotides 1-381), the terminator (nucleotides 382-759) and further 3' UTR (nucleotides 760-1193). In another embodiment, a genomic sequence encoding the rice Xa10 protein comprises the sequence set forth in SEQ ID NO:17 which includes the coding sequence (nucleotides 1-381), the terminator (nucleotides 382-759) and further 3' UTR (nucleotides 760-2215). In another embodiment, the rice Xa10 sequence comprises the sequence set forth in nucleotides 1-759 of SEQ ID NO:17 plus any number of nucleotides 3' of the terminator in SEQ ID NO:17 that are contiguous to the terminator. In one embodiment, the sequence of a synthetic Xa10 gene is set forth in SEQ ID NO:11. In another embodiment, the sequence of a synthetic Xa10 gene is set forth in SEQ ID NO:12.

In one embodiment, the rice Xa10 sequence comprises the sequence set forth in nucleotides 1-381 of SEQ ID NO:17 plus any number of nucleotides 3' of the stop codon in SEQ ID NO:17 that are contiguous to the stop codon. In one embodiment, the Xa10 sequence comprises nucleotides 1-420 of the sequence set forth in SEQ ID NO:17. In another embodiment, the Xa10 sequence comprises nucleotides 1-625 of the sequence set forth in SEQ ID NO:17. In an additional embodiment, the Xa10 sequence comprises nucleotides 1-852 of the sequence set forth in SEQ ID NO:17. In a further embodiment, the Xa10 sequence comprises nucleotides 1-1178 of the sequence set forth in SEQ ID NO:17. In another embodiment, the Xa10 sequence comprises nucleotides 1-1643 of the sequence set forth in SEQ ID NO:17. In and additional embodiment, the Xa10 sequence comprises nucleotides 1-2011 of the sequence set forth in SEQ ID NO:17. In a further embodiment, the Xa10 sequence comprises nucleotides 1-2211 of the sequence set forth in SEQ ID NO:17. These examples of Xa10 sequences are exemplary only and illustrate that the inventors contemplate any Xa10 sequence comprising 382-2215 contiguous nucleotides of SEQ ID NO:17 that must include nucleotides 1-381 of SEQ ID NO:17.

In one embodiment, the rice Xa10 sequence comprises the sequence set forth in nucleotides 1-759 of SEQ ID NO:17 which includes the coding sequence (nucleotides 1-381) and the terminator (nucleotides 382-759) plus any number of nucleotides 3' of the terminator in SEQ ID NO:17 that are contiguous to the terminator. In one embodiment, the Xa10 sequence comprises nucleotides 1-820 of the sequence set forth in SEQ ID NO:17. In another embodiment, the Xa10 sequence comprises nucleotides 1-1095 of the sequence set forth in SEQ ID NO:17. In an additional embodiment, the Xa10 sequence comprises nucleotides 1-1587 of the sequence set forth in SEQ ID NO:17. In a further embodiment, the Xa10 sequence comprises nucleotides 1-2050 of the sequence set forth in SEQ ID NO:17. These examples of Xa10 sequences are exemplary only and illustrate that the inventors contemplate any Xa10 sequence comprising the Xa10 coding sequence and terminator which comprises 760-2215 contiguous nucleotides of SEQ ID NO:17 that must include nucleotides 1-759 of SEQ ID NO:17.

In a third aspect, the present invention provides a vector as described herein comprising a synthetic Xa10 gene described herein. Such vectors are well known to the skilled artisan or described further below. The present invention also provides a plant cell comprising the vector and a transgenic plant having broad-spectrum resistance to bacterial blight comprising the plant cell. In one embodiment, the plant cell is a rice cell. In another embodiment, the transgenic plant is a transgenic rice plant.

In a fourth aspect, the present invention provides a method of making a transgenic plant having broad-spectrum resistance to bacterial blight. In accordance with the present invention, the method comprises transfecting a synthetic Xa10 gene described herein or a vector comprising a synthetic Xa10 gene described herein into a plant cell or into plant cells and producing a transgenic plant from the transfected plant cell or transfected plant cells. In accordance with the present invention, the synthetic Xa10 gene is expressed in the transgenic plant. Transfecting the synthetic Xa10 gene or vector into a plant cell or into plant cells is also sometimes referred to herein as transforming a plant cell or plant cells with the synthetic Xa10 gene or vector. In one embodiment, the plant cell or cells is a rice cell or cells. Such methods are well known to the skilled artisan or described further below.

In a fifth aspect, the present invention provides a transgenic plant having at least one copy of a synthetic Xa10 gene described herein stably incorporated into its genome. In one embodiment, the transgenic plant contains two copies of the synthetic Xa10 gene. In another embodiment, the transgenic plant contains three copies of the synthetic Xa10 gene. In an additional embodiment, the transgenic plant contains four copies of the synthetic Xa10 gene. In a further embodiment, the transgenic plant contains five copies of the synthetic Xa10 gene. In another embodiment, the transgenic plant contains six copies of the synthetic Xa10 gene. In one embodiment, the plant is a rice plant. In another embodiment, the transgenic rice plant is referred to herein as the L2 plant or L2 line. The present invention also provides for a plant that contains a synthetic Xa10 gene described herein stably incorporated into its genome that is derived by crossing a transgenic plant described herein or its progeny with a second plant and selecting progeny that contain the synthetic Xa10 gene. In accordance with the present invention, the transgenic plant or plants of the present invention can be used in conventional breeding programs. In one embodiment, the transgenic plant used in a breeding program is the transgenic rice plant referred to herein as the L2 plant or L2 line or progeny thereof.

Generally, the vector or expression cassette may additionally comprise a selectable marker gene for the selection of transformed cells. Selectable marker genes are utilized for the selection of transformed cells or tissues. Usually, the plant selectable marker gene will encode antibiotic resistance, with suitable genes including at least one set of genes coding for resistance to the antibiotic spectinomycin, the streptomycin phosphotransferase (spt) gene coding for streptomycin resistance, the neomycin phosphotransferase (nptII) gene encoding kanamycin or geneticin resistance, the hygromycin phosphotransferase (hpt or aphiv) gene encoding resistance to hygromycin, acetolactate synthase (als) genes. Alternatively, the plant selectable marker gene will encode herbicide resistance such as resistance to the sulfonylurea-type herbicides, glufosinate, glyphosate, ammonium, bromoxynil, imidazolinones, and 2,4-dichlorophenoxyacetate (2,4-D), including genes coding for resistance to herbicides which act to inhibit the action of glutamine synthase such as phosphinothricin or basta (e.g., the bar gene). See generally, International Publication Nos. WO 02/36782 and WO 2008/094127, U.S. Pat. No. 7,205,453 and U.S. Patent Application Publication Nos. 2006/0218670, 2006/0248616, 2007/0143880 and 2009/0100536, and the references cited therein. See also, Jefferson et al. (1991); De Wet et al. (1987); Goff et al. (1990); Kain et al. (1995) and Chiu et al. (1996). This list of selectable marker genes is not meant to be limiting. Any selectable marker gene can be used. The selectable marker gene is also under control of a promoter operable in the plant species to be transformed. Such promoters include those described in International Publication No. WO 2008/094127, U.S. Patent Application Publication No. 2012/0245339, and the references cited therein. See also, U.S. Patent Application Publication Nos. 2008/0313773 and 2010/0199371 for an exemplification of additional markers that can be used in accordance with the present invention.

Alternatively, the vector or expression cassette may additionally comprise a Cre-lox recombination marker free system, such as described herein. Such a system is useful for producing selection marker free transgenic plants.

In preparing the vector or expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g. transitions and transversions may be involved.

Once a nucleic acid, such as a synthetic Xa10 gene described herein, has been cloned into a vector or an expression vector, it may be introduced into a plant cell using conventional transformation procedures. The term "plant cell" is intended to encompass any cell derived from a plant including undifferentiated tissues such as callus and suspension cultures, as well as plant seeds, pollen or plant embryos. Plant tissues suitable for transformation include leaf tissues, root tissues, meristems, protoplasts, hypocotyls, cotyledons, scutellum, shoot apex, root, immature embryo, pollen, and anther. "Transformation" means the directed modification of the genome of a cell by the external application of recombinant DNA from another cell of different genotype, leading to its uptake and integration into the subject cell's genome. In this manner, genetically modified plants, plant cells, plant tissue, seed, and the like can be obtained.

The nucleic acids, vectors or constructs may be introduced into the genome of the desired plant host by a variety of conventional techniques. Techniques for transforming a wide variety of higher plant species are well known and described in the technical and scientific literature. Transformation protocols may vary depending on the type of plant or plant cell, i.e., monocot or dicot, targeted for transformation, as is well known to the skilled artisan. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. Thus, any method, which provides for effective transformation/transfection may be employed. See, for example, U.S. Pat. Nos. 7,241,937, 7,273,966 and 7,291,765 and U.S. Patent Application Publication Nos. 2007/0231905 and 2008/0010704 and references cited therein. See also, International Published Application Nos. WO 2005/103271, WO 2005/017158, WO 2008/094127, WO 2012/033462 and references cited therein.

Transformed plant cells which are derived by any of the above transformation techniques can be cultured to regenerate a whole plant which possesses the transformed genotype and thus the desired phenotype, e.g., a transgenic plant. A "transgenic plant" is a plant into which foreign DNA has been introduced. A "transgenic plant" encompasses all descendants, hybrids, and crosses thereof, whether reproduced sexually or asexually, and which continue to harbor the foreign DNA. Regeneration techniques rely on manipulation of certain phytohormones in a tissue culture growth medium, typically relying on a biocide and/or herbicide marker which has been introduced together with the desired nucleotide sequences. See for example, International Published Application No. WO 2008/094127 and references cited therein.

The foregoing methods for transformation are typically used for producing a transgenic variety in which the expression cassette is stably incorporated. After the expression cassette is stably incorporated in transgenic plants, it can be transferred to other plants by sexual crossing. In one embodiment, the transgenic variety could then be crossed, with another (non-transformed or transformed) variety, in order to produce a new transgenic variety. Alternatively, a genetic trait which has been engineered into a particular cotton line using the foregoing transformation techniques could be moved into another line using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties which do not contain that gene. As used herein, "crossing" can refer to a simple X by Y cross, or the process of backcrossing, depending on the context. Any of a number of standard breeding techniques can be used, depending upon the species to be crossed.

Once transgenic plants of this type are produced, the plants themselves can be cultivated in accordance with conventional procedures. Transgenic seeds can, of course, be recovered from the transgenic plants. These seeds can then be planted in the soil and cultivated using conventional procedures to produce transgenic plants. The cultivated transgenic plants will express the synthetic Xa10 gene to provide broad-spectrum resistance to bacterial blight. The cultivated transgenic plants can also be used in conventional breeding programs to derive additional plants that will express the synthetic Xa10 gene to provide broad-spectrum resistance to bacterial blight.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, *Molecular Cloning* (Cold Spring Harbor Laboratory Press, Cold Spring Harbor, N.Y.); Sambrook et al., 1989, *Molecular Cloning,* 2nd Ed. (Cold Spring Harbor Laboratory Press, Cold Spring Harbor, N.Y.); Sambrook and Russell, 2001, *Molecular Cloning,* 3rd Ed. (Cold Spring Harbor Laboratory Press, Cold Spring Harbor, New York); Green and Sambrook, 2012, *Molecular Cloning,* 4th Ed. (Cold Spring Harbor Laboratory Press, Cold Spring Harbor, N.Y.); Ausubel et al., 1992, *Current Protocols in Molecular Biology* (John Wiley & Sons, including periodic updates); Glover, 1985, *DNA Cloning* (IRL Press, Oxford); Russell, 1984, *Molecular biology of plants: a laboratory course manual* (Cold Spring Harbor Laboratory Press, Cold Spring Harbor, N.Y.); Anand, *Techniques for the Analysis of Complex Genomes*, (Academic Press, New York, 1992); Guthrie and Fink, *Guide to Yeast Genetics and Molecular Biology* (Academic Press, New York, 1991); Harlow and Lane, 1988, *Antibodies*, (Cold Spring Harbor Laboratory Press, Cold Spring Harbor, N.Y.); *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); Riott, *Essential Immunology,* 6th Edition, Blackwell Scientific Publications, Oxford, 1988; Fire et al., *RNA Interference Technology: From Basic Science to Drug Development*, Cambridge University Press, Cambridge, 2005; Schepers, *RNA Interference in Practice*, Wiley-VCH, 2005; Engelke, *RNA Interference (RNAi): The Nuts & Bolts of siRNA Technology*, DNA Press, 2003; Gott, *RNA Interference, Editing, and Modification: Methods and Protocols (Methods in Molecular Biology)*, Human Press, Totowa, N.J., 2004; Sohail, *Gene Silencing by RNA Interference: Technology and Application*, CRC, 2004.

EXAMPLES

The present invention is described by reference to the following Examples, which is offered by way of illustration and is not intended to limit the invention in any manner. Standard techniques well known in the art or the techniques specifically described below were utilized.

Example 1

Materials and Methods

TAL Effectors and *Xanthomonas oryzae* pv. *Oryzae* (Xoo) Strains:

TAL effector genes, avrXa10, avrXa27, pthXo1, pthXo6 and pthXo7, have been reported previously (Hopkins et al., 1992; Gu et al., 2005; Yang et al., 2006; Sugio et al., 2007). TAL effector genes were cloned into vector pBluescript and placed under lacZ promoter. The intermediate construct were then fused with cosmid vector pHM1 (GenBank Accession No. EF059993) at the Hind III site. Cosmid constructs carrying the TAL effectors were introduced into *X. oryzae* pv. *oryzae* strain 1947 by electroporation. Twenty-eight field strains of *X. oryzae* pv. *oryzae*, which were collected from 11 countries were used in this study.

Plants and Growth Conditions:

IRBB10A is an improved near-isogenic line (NIL) of Xa10 in the IR24 genetic background (Gu et al., 2008). Nipponbare is a japonica rice cultivar. Rice plants, including transgenic plants, were grown in a greenhouse at a temperature of 32° C. and 25° C. for 12.5 h (light) and 11.5 h (dark), respectively.

Binary Construct:

Binary construct pCXA10E5 carrying $Xa10^{E5}$ (FIG. 1) was made based on pCAS4671, which harbors 4671-bp AvrII-SacI genomic clone of Xa10 in binary vector pC1300. A 661-bp synthetic BamHI-NruI DNA fragment containing $EBE_{pthXo7}$, $EBE_{pthXo1}$, $EBE_{AvrXa10}$, $EBE_{pthXo6}$ and $EBE_{AvrXa27}$ were used to replace the 657-bp BamHI-NruI fragment in the native promoter of Xa10 gene. The pCXA10E5 was introduced into *Agrobacterium tumefaciens* strain AGL1 by electroporation.

Rice Transformation:

*Agrobacterium*-mediated transformation of Nipponbare was carried out using the method described previously (Hiei et al., 1994) with slight modification. Briefly, vigorously growing embryogenic calli derived from the scutellum of mature embryos was co-cultured with *A. tumefaciens* strains harbouring binary plasmids for 2 days. After co-culture, the rice tissues were washed and then cultured on selection medium comprising NB basal medium ($NB_0$ medium; contains the macronutrients described by Chu (1975) and the micronutrients described by Gamborg et al. (1968)) containing 2 mg/L 2,4-dichlorophenoxyacetic acid (2,4-D), 250 mg/L cefotaxime and 50 mg/L hygromycin at 26° C. in the dark. After 4 weeks selection, the hygromycin-resistant calli were excised from co-cultivated callus and transferred to regeneration medium comprising $NB_0$ medium containing 2.0 mg/L kinetin (KT), 0.02 mg/L α-naphthaleneacetic acid (NAA) and 50 mg/L hygromycin. Three weeks later the regenerated hygromycin-resistant plantlets were transferred to plantlet medium comprising ½ strength MS basal medium (½ $MS_0$ medium; MS basal medium defined by Murashige and Skoog (1962)) containing 50 mg/L hygromycin for shoot and root elongation. Regenerated plantlets were subsequently transplanted to the soil in pots and grown in a greenhouse.

Bacterial Blight Inoculation and Disease Scoring:

Bacterial inoculation was carried out using the leaf-clipping method (Kauffman et al., 1973). Briefly, *X. oryzae* pv. *oryzae* strains were grown on PSA medium (10 g/l peptone, 10 g/l sucrose, 1 g/l glutamic acid, 16 g/l bacto-agar, and pH 7.0) for 2 days at 28° C. The bacterial cells were collected and re-suspended in sterile water at an optical density of 0.5 at OD600. The bacterial cell suspension was applied to the two youngest, but fully expanded, leaves of each tiller by clipping 5-6 cm, from the tip of the leaf using a pair of scissors dipped in the inoculum. Lesion length (LL) was measured 2 weeks after inoculation. The disease symptom was scored as resistant (R, LL≤3.0 cm), moderately resistant (MR, 3.0 cm<LL≤6.0 cm), moderately susceptible (MS, 6.0 cm<LL≤9.0 cm) and susceptible (S, LL>9.0 cm) (Gu et al., 2004).

Southern Blot Analysis:

Rice genomic DNA was isolated from leaf tissues according to the procedures described previously (Dellaporta et al., 1983). About 2 μg of DNA was digested with the appropriate restriction enzymes, separated on 0.8% agarose gel and blotted to Hybond™-N+nylon membrane (Amersham Biosciences, GE healthcare, USA). DNA hybridization was conducted according to standard procedures (Sambrook et al., 1989). DNA probes were labeled with DIG system (Roche Applied Science, USA). The DNA probe for the Hpt gene was amplified by PCR using DNA primers Hpt-F (5'AAAAAGCCTGAACTCACC GCG3'; SEQ ID NO:18) and Hpt-R (5'TACTTCTACACAGCCATCGGT3'; SEQ ID NO:19). The DNA probe for the Xa10 gene was amplified by PCR using DNA primers Xa10-F (5'CACGGGCCCCCTC-CTGTTTGC3'; SEQ ID NO:20) and Xa10-R (5'CCTCGTCGTCTTCA CCAATGCAG3'; SEQ ID NO:21). The primers used for recovering the $Xa10^{E5}$ gene from the L2 line were Seq F5 (5'CTAGGTTTATTGGCT-GAGCAATG3'; SEQ ID NO:22); Seq R5 (5'TCTAACT-GTCGCCGATCTGCTG3'; SEQ ID NO:23), Seq F4 (5'TTCTTCTTCCTTCCT CTCTCTAC3'; SEQ ID NO:24), Seq R4 (5'TCACTCGCCATGTCTCTACTTC3'; SEQ ID NO:25), Seq F3 (5'AGGAAAGGTGAGAAGGGAATTG3'; SEQ ID NO:26), Seq R3 (5'GTTT AGCTCGACTTTC-GACCCAG3'; SEQ ID NO:27), 4686F (5'CTGGGTC-GAAAGTCGAGCT AAAC3'; SEQ ID NO:28), Xa10H5R (5'CCATCGTGATATATATGGGCCTCAGACG3'; SEQ ID NO:29), Seq F1 (5'GCCATACTCTTCTACCTCTCTG3'; SEQ ID NO:30), Seq R1 (5'TTATTCTTTTCATATCATTT-GATTC3'; SEQ ID NO:31), Seq F2 (5'GTAAAACTATAT GTGTACATGG3'; SEQ ID NO:32) and Seq R2 (5'TC-CTCGCTAAATTAAAGTGATG3'; SEQ ID NO:33).

Quantitative reverse-transcription PCR (qRT-PCR): qRT-PCR was carried out in accordance with the procedures described previously (Gu et al., 2011) using a CFX96 real-time PCR system (Bio-Rad). Total RNA was extracted from rice leaves at 24 hours post inoculation (hpi) with *X. oryzae* pv. *oryzae* strains. The total RNA samples were first treated with DNase I, and then reversely transcribed to first-strand cDNAs using iScript cDNA synthesis kit (Bio-Rad) according to the manufacturer's instructions. To ensure maximum specificity and efficiency during quantitative PCR, oligo primers were further tested for linearity by constructing standard curves on five or six serial 10-fold dilutions. A standard reaction mixture (15 μl) contained 2 μl cDNA template, 1× SsoFast EvaGreen supermix (Bio-Rad) and 500 nM forward and reverse primers. The PCR reaction was conducted at an initial denaturing step of 98° C. for 3 min, followed by 40 cycles of 98° C. for 5 s, 55° C. for 5 s. A melting-curve reaction was subsequently performed for 5 s, starting at 75° C. with 0.2° C. increments. PCR product specificity was confirmed by melting-curve analysis and separation on a 2% agarose gel to ensure that the PCR reactions were free of primer dimers. The rice ubiquitin gene 1 (Ubi1) was used as an internal reference to normalize the relative amount of total RNA for all samples. The qRT-PCR experiments were repeated for three times. Rice Ubi gene was used as an internal control. The specific primers for Xa10 were 10RTF2 (5'GGCATCATCTTCTCCGGCG3'; SEQ ID NO:34) and 10RTR2 (5'GCAGC-TATACGGGCATAAG3'; SEQ ID NO:35). The specific primers for Ubi1 were RBQ3 (5'CCAGTAAGTCCTCAGC-CATG3'; SEQ ID NO:36) and RBQ4 (5'TTTC AGACAC-CATCAAACCAG3'; SEQ ID NO:37).

Example 2

Production of Transgenic Lines Carrying $Xa10^{E5}$

Transgenic rice plants were produced by *Agrobacterium*-mediated transformation of Nipponbare (Hiei et al., 1994). After one month subculture of co-cultivated calli on selective medium, 1,896 hyromycin-resistant calli were obtained.

However, most of the hyromycin-resistant calli turned brown and eventually died after they were transferred onto regeneration medium and cultured under light. Only a few of the hyromycin-resistant calli remained healthy and eventually regenerated transgenic plantlets. Finally, 8 independent transgenic lines were obtained. Some lines might have more than one $T_0$ plants derived from a single transformed cell. $T_0$ plants were transplanted to soil and grown in greenhouse.

Five-week-old $T_0$ plants were inoculated with *X. oryzae* pv. *oryzae* strain 1947 expressing AvrXa10. Disease evaluation at two weeks after bacterial blight inoculation indicated that only $T_0$ plants from two lines, L2 and L5, conferred complete resistance to 1947(pHM1AvrXa10). Other $T_0$ plants were susceptible to the Xa10-incompatible strain. Eight $T_0$ plants of L2 were obtained and they all displayed normal morphological phenotype and growth duration compared to that of wild-type plants. One $T_0$ plant of L5 was obtained and the plant showed slightly stress-related phenotypes, such as stiff leaves and longer growth duration, compared to that of wild-type. The stress-related phenotypes were more severe in homozygote in the $T_2$ or $T_3$ generations. L5 was abandoned for further study.

Figure 2:
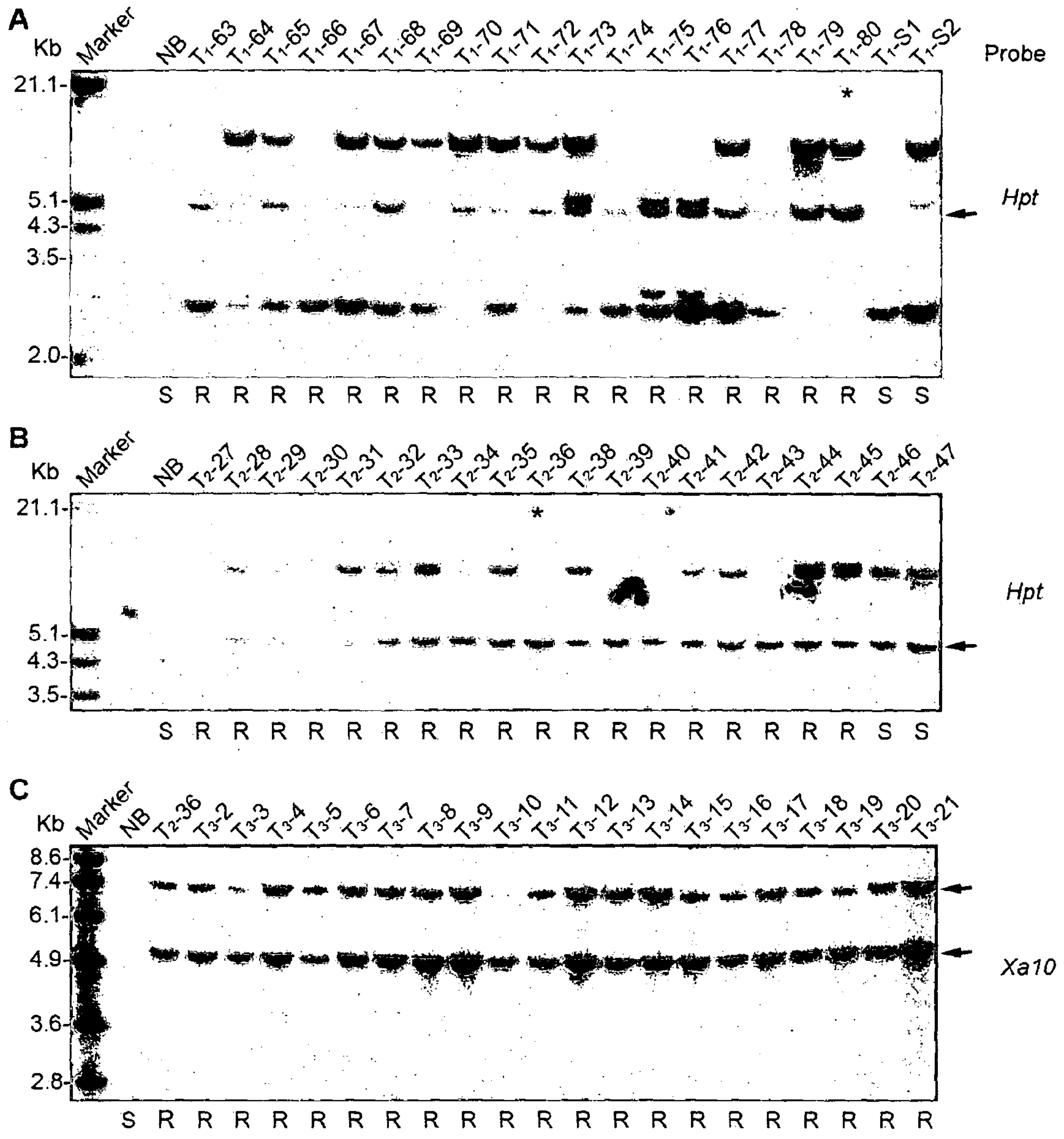
FIGS. 2A-2C show Southern blot analysis of transgenic plants of L2 line.

There were at least 6 copies of T-DNA in the $T_0$ plants of L2 detected by Southern blot analysis using Hpt probe. They could be separated in the $T_1$ generation (FIG. 2A). However, only one copy of T-DNA, which showed the hybridized band at about 5.0 kb detected by Hpt probe, carried functional $Xa10^{E5}$ gene and co-segregated with the resistant phenotype. $T_2$ plants that only carried the functional $Xa10^{E5}$ gene were obtained from $T_2$ progeny of $T_1$-80 (FIG. 2B). One of the $T_2$ plants, $T_2$-36 carried homozygous $Xa10^{E5}$ gene. $T_2$-36 had two copies of $Xa10^{E5}$ gene with hybridized bands at about 5.2 kb and 7.4 kb, respectively, detected by Xa10 probe (FIG. 2C). The two hybridized bands were greater than the expected 2866-bp band of the BamHI-XbaI fragment from the $Xa10^{E}$ gene (FIG. 1). In addition, the two copies of $Xa10^{E5}$ gene co-segregated in the subsequent generation (FIG. 2C). The results indicated that the two copies of $Xa10^{E5}$ gene were parts of the two truncated T-DNAs which were integrated into Nipponbare genome in the same or closely-related location after illegitimate T-DNA integration. The intact $Xa10^{E5}$ gene, consisting of the $Xa10^{E5}$ promoter (2456 bp), the Xa10 coding region (381-bp), the Xa10 terminator (378 bp) and a 434-bp 3' region flanking the Xa10 terminator, were recovered from the $T_2$-36 plant and its progeny by PCR amplification and DNA sequencing. The genomic sequence of $Xa10^{E5}$ recovered from L2 is set forth in SEQ ID NO:12. The regions of the genomic sequence of $Xa10^{E5}$ are as follows: nucleotides 1-2456 is a $Xa10^{E5}$ promoter; nucleotides 2457-2837 is the Xa10 ORF; nucleotides 2838-3215 is a Xa10 terminator; and nucleotides 3216-3649 is a 3' region flanking the Xa10 terminator. $T_2$-36 progeny were still designated as L2 that carries functional $Xa10^{E5}$ genes for the further studies.

Example 3

Figure 3:
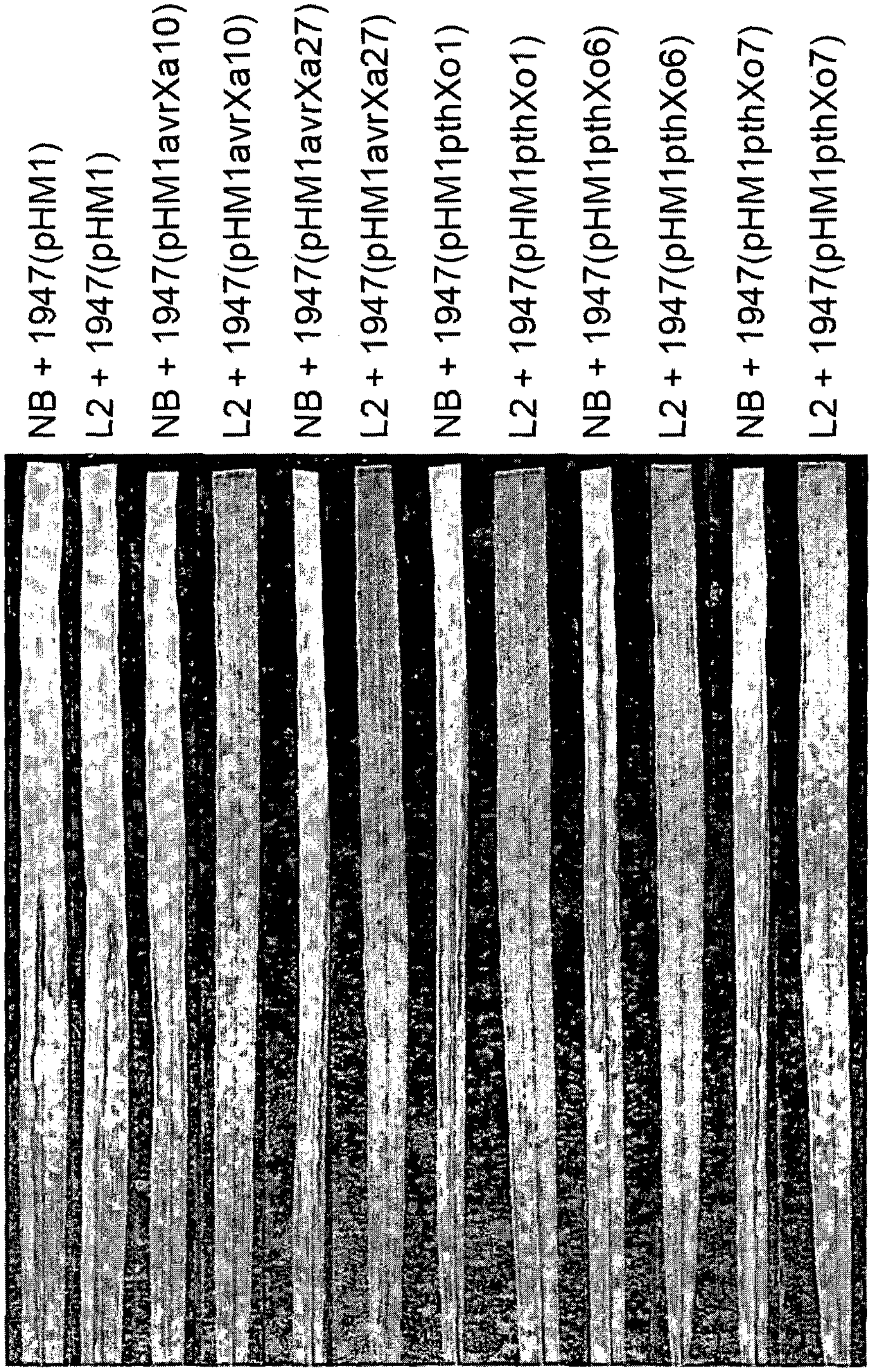
FIG. 3 shows bacterial blight phenotype of L2 plants. Six-week-old $T_3$ plants carrying homozygous $Xa10^{E5}$, which was derived from $T_2$-36 plant of L2, were inoculated with *X. oryzae* pv. *oryzae* strain 1947 expressing TAL effectors AvrXa10, AvrXa27, pthXo1, pthX06 pthXo7 or empty vector pHM1. Image was taken at 2 weeks after inoculation. Nipponbare (NB) was used as the susceptible control.
Figure 4:
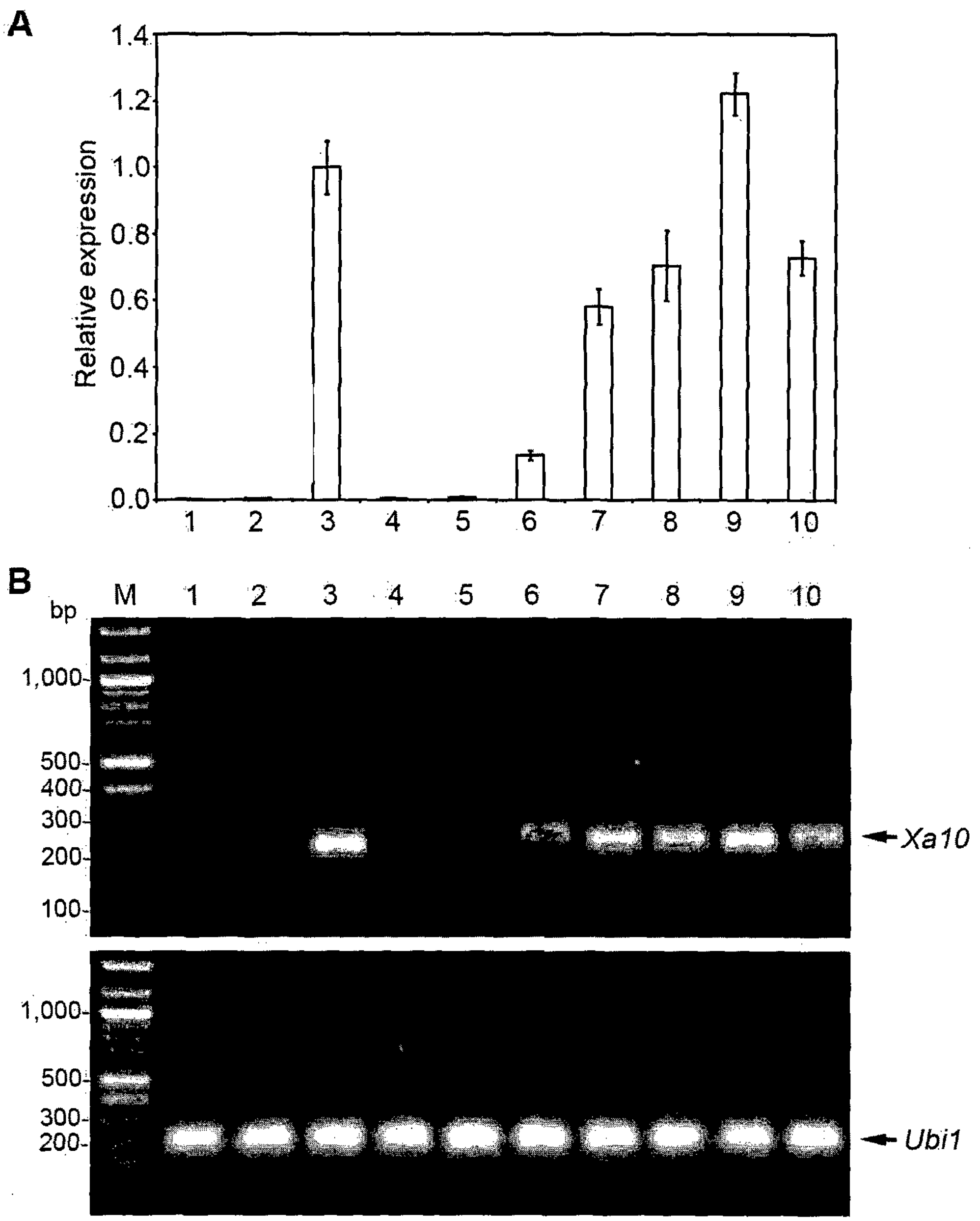
FIGS. 4A and 4B show the induction of Xa10 in IRBB10A and L2 plants upon inoculation with *X. oryzae* pv. *oryzae* strains.

$Xa10^{E5}$ was Induced by *X. oryzae* pv. *Oryzae* Strains Expressing the Corresponding TAL Effectors L2 plants conferred resistance to *X. oryzae* pv. *oryzae* strains 1947(pHM1avrXa10), 1947(pHM1avrXa27), 1947 (pHM1pthXo1), 1947 (pHM1pthXo6) and 1947 (pHM1pthXo7), whereas Nipponbare plants were susceptible to all these strains (FIG. 3). In control experiments, both L2 and Nipponbare were susceptible to *X. oryzae* pv. *oryzae* strain 1947 (FIG. 3).

qRT-PCR analysis indicated that the $Xa10^{E5}$ gene in L2 plants was activated after inoculation with incompatible *X. oryzae* pv. *oryzae* strains (FIG. 4). The expression levels of Xa10 transcripts in L2 plants inoculated with 1947 (pHM1avrXa27), 1947(pHM1pthXo1), 1947 (pHM1pthXo6) or 1947(pHM1pthXo7) were comparable to that of Xa10 transcripts in IRBB10A plants inoculated with 1947(pHM1avrXa10) (FIG. 4). The expression level of Xa10 transcripts in L2 plants inoculated with 1947 (pHM1avrXa10) was only 13% to that of Xa10 transcripts in IRBB10A plants inoculated with 1947(pHM1avrXa10) (FIG. 4), which was still sufficient to provide complete resistance to the incompatible strain (FIG. 3). Likewise in IRBB10A plants, the Xa10 transcript was not detected in the L2 plants after mock inoculation or inoculation with 1947 (pHM1) (FIG. 4).

Example 4

$Xa10^{E5}$ Conferred Broad Spectrum Resistance to Multiple Field Strains Collected from Different Countries Twenty-eight field strains of *X. oryzae* pv. *oryzae* (Xoo) collected from different rice growing countries around the world (Table 1) were used to test the resistant spectrum of $Xa10^{E5}$ in L2 plants to bacterial blight disease. Non-transgenic Nipponbare plants were susceptible or moderate susceptible to most of the *X. oryzae* pv. *oryzae* strains tested and only showed moderate resistance to GD1358 from China and CIAT1185 from Columbia (Table 1). IRBB10A is an improved near-isogenic line of Xa10 in IR24 genetic background (Gu et al., 2008). IRBB10A only showed complete resistance to PXO86(R2) and PXO112(R5), and moderate resistance to Aust-2031 and Aust-R3 (Table 1 and (Gu et al., 2008)). The L2 plants conferred high and broad-spectrum resistance to 27 Xoo strains tested except for 1947, an *X. oryzae* pv. *oryzae* strain from Africa (Table 1).

TABLE 1

Resistant Spectrum of $Xa10^{E5}$ L2 to Xoo Strains Collected from Different Countries

| | | Lesion length and resistance score[a] | | | |
|---|---|---|---|---|---|
| Xoo Strain | Origin | IR24 | IRBB10A | NB | L2 |
| 1947 | Africa | 27.0 ± 6.3 (S) | 28.6 ± 4.8 (S) | 15.8 ± 3.8 (S) | 10.1 ± 0.9 (S) |
| Aust-2031 | Australia | 5.5 ± 1.4 (MR) | 4.4 ± 1.6 (MR) | 9.4 ± 1.8 (S) | 0.2 ± 0.1 (R) |
| Aust-R3 | Australia | 5.7 ± 1.5 (MR) | 6.8 ± 2.0 (MR) | 10.9 ± 4.2 (S) | 0.1 ± 0.0 (R) |
| GD1358 | China | 19.0 ± 7.3 (S) | 21.1 ± 3.6 (S) | 4.0 ± 1.6 (MR) | 0.1 ± 0.0 (R) |
| HB17 | China | 25.3 ± 3.8 (S) | 24.7 ± 4.0 (S) | 21.2 ± 2.0 (S) | 0.1 ± 0.0 (R) |

TABLE 1-continued

Resistant Spectrum of Xa10$^{E5}$ L2 to Xoo Strains Collected from Different Countries

| | | Lesion length and resistance score[a] | | | |
|---|---|---|---|---|---|
| Xoo Strain | Origin | IR24 | IRBB10A | NB | L2 |
| HB21 | China | 19.6 ± 2.6 (S) | 15.2 ± 3.5 (S) | 20.8 ± 1.7 (S) | 0.1 ± 0.0 (R) |
| HLJ72 | China | 10.0 ± 2.5 (S) | 9.8 ± 3.0 (S) | 12.1 ± 1.3 (S) | 0.1 ± 0.0 (R) |
| JS49-6 | China | 24.6 ± 3.6 (S) | 21.6 ± 4.0 (S) | 18.3 ± 2.6 (S) | 0.1 ± 0.0 (R) |
| LN57 | China | 22.1 ± 2.8 (S) | 25.4 ± 3.5 (S) | 20.1 ± 4.8 (S) | 0.1 ± 0.0 (R) |
| NX42 | China | 23.3 ± 4.7 (S) | 23.2 ± 4.8 (S) | 20.6 ± 2.2 (S) | 0.1 ± 0.0 (R) |
| ZHE173 | China | 21.8 ± 3.9 (S) | 23.0 ± 4.5 (S) | 14.5 ± 2.8 (S) | 0.1 ± 0.0 (R) |
| CIAT1185 | Columbia | 18.1 ± 4.8 (S) | 13.6 ± 3.5 (S) | 4.6 ± 2.1 (MR) | 0.1 ± 0.0 (R) |
| A3842 | India | 22.4 ± 3.8 (S) | 21.5 ± 3.9 (S) | 16.6 ± 3.4 (S) | 0.1 ± 0.0 (R) |
| A3857 | India | 19.1 ± 2.7 (S) | 18.3 ± 4.6 (S) | 19.0 ± 1.9 (S) | 0.1 ± 0.0 (R) |
| IXO56 | Indonesia | 24.1 ± 5.2 (S) | 23.9 ± 3.6 (S) | 13.3 ± 2.5 (S) | 0.1 ± 0.0 (R) |
| H75373 | Japan | 25.7 ± 5.7 (S) | 24.4 ± 4.3 (S) | 17.9 ± 2.0 (S) | 0.1 ± 0.0 (R) |
| T7174 | Japan | 23.3 ± 3.6 (S) | 19.1 ± 3.0 (S) | 19.7 ± 2.1 (S) | 0.2 ± 0.1 (R) |
| JW89011 | Korea | 23.8 ± 5.1 (S) | 26.6 ± 5.1 (S) | 16.7 ± 2.3 (S) | 0.1 ± 0.0 (R) |
| K202 | Korea | 25.6 ± 3.9 (S) | 26.3 ± 4.3 (S) | 12.3 ± 2.3 (S) | 0.1 ± 0.0 (R) |
| NXO260 | Nepal | 22.4 ± 3.4 (S) | 22.4 ± 4.5 (S) | 16.6 ± 2.0 (S) | 0.1 ± 0.0 (R) |
| PXO86(R2) | Philippines | 21.9 ± 3.1 (S) | 0.2 ± 0.1 (R) | 12.7 ± 2.1 (S) | 0.1 ± 0.0 (R) |
| PXO79(R3) | Philippines | 23.1 ± 4.3 (S) | 20.2 ± 4.1 (S) | 6.7 ± 2.3 (MS) | 0.1 ± 0.0 (R) |
| PXO71(R4) | Philippines | 23.1 ± 3.3 (S) | 23.2 ± 4.7 (S) | 15.9 ± 1.8 (S) | 0.1 ± 0.0 (R) |
| PXO112(R5) | Philippines | 13.4 ± 2.5 (S) | 0.1 ± 0.0 (R) | 11.8 ± 3.1 (S) | 0.1 ± 0.0 (R) |
| PXO113(R4) | Philippines | 18.5 ± 2.1 (S) | 18.6 ± 3.7 (S) | 11.0 ± 3.6 (S) | 0.1 ± 0.0 (R) |
| PXO99(R6) | Philippines | 23.4 ± 3.3 (S) | 23.2 ± 2.9 (S) | 14.2 ± 3.1 (S) | 0.1 ± 0.0 (R) |
| 2 | Thailand | 25.4 ± 3.6 (S) | 26.4 ± 3.9 (S) | 18.6 ± 4.4 (S) | 0.1 ± 0.0 (R) |
| R7 | Thailand | 10.0 ± 6.5 (S) | 6.9 ± 2.7 (MS) | 9.9 ± 2.3 (S) | 0.1 ± 0.0 (R) |

[a]Six-Week-old rice plants were inoculated with *X. oryzae* pv. *oryzae* strains. Lesion length and disease phenotype of the inoculated plants were scored at two weeks after inoculation.
For disease scoring:
R, resistant, lesion length ≤3.0 cm;
MR, moderately resistant, lesion length >3.0 cm and ≤6.0 cm;
MS, moderately susceptible, lesion length >6.0 cm and ≤9.0 cm;
S, susceptible, lesion length >9.0 cm.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

It will be appreciated that the methods and compositions of the instant invention can be incorporated in the form of a variety of embodiments, only a few of which are disclosed herein. Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

BIBLIOGRAPHY

Alfano, J. R., and Collmer, A. (2004). Type III secretion system effector proteins: double agents in bacterial disease and plant defense. Annu Rev Phytopathol 42, 385-414.

Antony, G., Zhou, J., Huang, S., Li, T., Liu, B., White, F., and Yang, B. (2010). Rice xa13 recessive resistance to bacterial blight Is defeated by induction of the disease susceptibility gene Os-11N3. Plant Cell 22, 3864-3876.

Boch, J., and Bonas, U. (2010). *Xanthomonas* AvrBs3 family-type III effectors: discovery and function. Annu Rev Phytopathol 48, 419-436.

Boch, J., Scholze, H., Schornack, S., Landgraf, A., Hahn, S., Kay, S., Lahaye, T., Nickstadt, A., and Bonas, U. (2009). Breaking the code of DNA binding specificity of TAL-type III effectors. Science 326, 1509-1512.

Bogdanove, A. J., Schornack, S., and Lahaye, T. (2010). TAL effectors: finding plant genes for disease and defense. Curr Opin Plant Biol 13, 394-401.

Bonas, U., Stall, R. E., and Staskawicz, B. (1989). Genetic and structural characterization of the avirulence gene avrBs3 from *Xanthomonas campestris* pv. *vesicatoria*. Mol Gen Genet 218, 127-136.

Chen, L. Q., Hou, B. H., Lalonde, S., Takanaga, H., Hartung, M. L., Qu, X. Q., Guo, W. J., Kim, J. G., Underwood, W., Chaudhuri, B., Chermak, D., Antony, G., White, F. F., Somerville, S. C., Mudgett, M. B., and Frommer, W. B.

(2010). Sugar transporters for intercellular exchange and nutrition of pathogens. Nature 468, 527-532.

Chu C. C. et al. (1975). Establishment of an efficient medium for anther culture of rice through comparative experiments on the nitrogen sources. Scienta Sinica 18, 659-668.

Dellaporta, S. L., Wood, J., and Hicks, J. B. (1983). A plant DNA minipreparation: version II. Plant Molecular Biology Reporter 1, 19-21.

Gamborg, O. L., Miller, R. A., Ojima, K. (1968). Nutrient requirements of suspension cultures of soybean root cells. Exp Cell Res 50, 151-158.

Gu, K., Tian, D., Yang, F., Wu, L., Sreekala, C., Wang, D., Wang, G. L., and Yin, Z. (2004). High-resolution genetic mapping of Xa27(t), a new bacterial blight resistance gene in rice, *Oryza sativa L*. Theor Appl Genet 108, 800-807.

Gu, K., Yang, B., Tian, D., Wu, L., Wang, D., Sreekala, C., Yang, F., Chu, Z., Wang, G. L., White, F. F., and Yin, Z. (2005). R gene expression induced by a type-III effector triggers disease resistance in rice. Nature 435, 1122-1125.

Gu, K., Sangha, J. S., Li, Y., and Yin, Z. (2008). High-resolution genetic mapping of bacterial blight resistance gene Xa10. Theor Appl Genet 116, 155-163.

Gu, K., Tian, D., Qiu, C., and Yin, Z. (2009). Transcription activator-like type III effector AvrXa27 depends on OsTFIIAgamma5 for the activation of Xa27 transcription in rice that triggers disease resistance to *Xanthomonas oryzae* pv. *oryzae*. Mol Plant Pathol 10, 829-835.

Gu, K., Chiam, H., Tian, D., and Yin, Z. (2011). Molecular cloning and expression of heteromeric ACCase subunit genes from Jatropha curcas. Plant Sci 180, 642-649.

Herbers, K., Conradsstrauch, J., and Bonas, U. (1992). Race-specificity of plant-resistance to bacterial spot disease determined by repetitive motifs in a bacterial avirulence protein. Nature 356, 172-174.

Heuer, H., Yin, Y. N., Xue, Q. Y., Smalla, K., and Guo, J. H. (2007). Repeat domain diversity of avrBs3-like genes in *Ralstonia solanacearum* strains and association with host preferences in the field. Appl Environ Microbiol 73, 4379-4384.

Hiei, Y., Ohta, S., Komari, T., and Kumashiro, T. (1994). Efficient transformation of rice (*Oryza sativa* L.) mediated by *Agrobacterium* and sequence analysis of the boundaries of the T-DNA. Plant J 6, 271-282.

Hopkins, C. M., White, F. F., Choi, S. H., Guo, A., and Leach, J. E. (1992). Identification of a family of avirulence genes from *Xanthomonas oryzae* pv. *oryzae*. Mol Plant Microbe Interact 5, 451-459.

Iyer, A. S., and McCouch, S. R. (2004). The rice bacterial blight resistance gene xa5 encodes a novel form of disease resistance. Mol Plant Microbe Interact 17, 1348-1354.

Kauffman, H. E., Reddy, A. P. K., Hsieh, S. P. Y., and Merca, S. D. (1973). An improved technique for evaluating resistance to rice varieties of *Xanthomonas oryzae*. Plant Dis Rep 57, 537-541.

Kay, S., and Bonas, U. (2009). How *Xanthomonas* type III effectors manipulate the host plant. Curr Opin Microbiol 12, 37-43.

Kay, S., Hahn, S., Marois, E., Hause, G., and Bonas, U. (2007). A bacterial effector acts as a plant transcription factor and induces a cell size regulator. Science 318, 648-651.

Mew, T. W. V. C., C. M. Reyes, R. C. (1982). Interaction of *Xanthomonas campestris* pv. *oryzae* and a resistant rice cultivar. Phytopathology 72, 786-789.

Moscou, M. J., and Bogdanove, A. J. (2009). A simple cipher governs DNA recognition by TAL effectors. Science 326, 1501.

Murashige, T. and Skoog, F. (1962). A revised medium for rapid growth and bioassays with tobacco tissue cultures. Physiol Plant 15, 473-497.

Nino-Liu, D. O., Ronald, P. C., and Bogdanove, A. J. (2006). *Xanthomonas oryzae* pathovars: model pathogens of a model crop. Mol Plant Pathol 7, 303-324.

Romer, P., Hahn, S., Jordan, T., Strauss, T., Bonas, U., and Lahaye, T. (2007). Plant pathogen recognition mediated by promoter activation of the pepper Bs3 resistance gene. Science 318, 645-648.

Romer, P., Recht, S., and Lahaye, T. (2009). A single plant resistance gene promoter engineered to recognize multiple TAL effectors from disparate pathogens. Proc Natl Acad Sci USA 106, 20526-20531.

Sambrook, J., Fritsch, E., and Maniatis, T. (1989). Molecular Cloning: A Laboratory Manual, (1989) 2nd edn Cold Spring Harbor. N.Y. Cold Spring Harbor Laboratory., Sugio, A., Yang, B., Zhu, T., and White, F. F. (2007). Two type III effector genes of *Xanthomonas oryzae* pv. *oryzae* control the induction of the host genes OsTFIIAgamma1 and OsTFX1 during bacterial blight of rice. Proc Natl Acad Sci USA 104, 10720-10725.

Tian, D., and Yin, Z. (2009). Constitutive heterologous expression of avrXa27 in rice containing the R gene Xa27 confers enhanced resistance to compatible *Xanthomonas oryzae* strains. Mol Plant Pathol 10, 29-39.

White, F. F., Potnis, N., Jones, J. B., and Koebnik, R. (2009). The type III effectors of *Xanthomonas*. Mol Plant Pathol 10, 749-766.

Yang, B., and White, F. F. (2004). Diverse members of the AvrBs3/PthA family of type III effectors are major virulence determinants in bacterial blight disease of rice. Mol Plant Microbe Interact 17, 1192-1200.

Yang, B., Sugio, A., and White, F. F. (2005). Avoidance of host recognition by alterations in the repetitive and C-terminal regions of AvrXa7, a type III effector of *Xanthomonas oryzae* pv. *oryzae*. Mol Plant Microbe Interact 18, 142-149.

Yang, B., Sugio, A., and White, F. F. (2006). Os8N3 is a host disease-susceptibility gene for bacterial blight of rice. Proc Natl Acad Sci USA 103, 10503-10508.

Yoshimura, A., Mew, T. W., Khush, G. S., and Moura, T. (1983). Inheritance of resistance to bacterial blight in rice cultivar Cas 209. Phytopathology 73, 1409-1412.

Yoshimura, S., Yoshimura, A., Iwata, N., McCouch, S. R., Abenes, M. L., Baraoidan, M. R., Mew, T. W., and Nelson, R. J. (1995). Tagging and combining bacterial blight resistance genes in rice using RAPD and RFLP markers. Mol Breed 1, 375-387.

What is claimed is:

1. A plant promoter selected from the group consisting of:

(a) a plant promoter comprising the nucleotide sequence set forth in SEQ ID NO:2;

(b) a plant promoter consisting of the nucleotide sequence set forth in SEQ ID NO:2;

(c) a plant promoter consisting of the nucleotide sequence set forth in SEQ ID NO:10; and (d) a plant promoter comprising nucleotides 2208-2456 set forth in SEQ ID NO:10 and from 1-2207 contiguous nucleotides set forth in SEQ ID NO:10 that are 5' to and contiguous with nucleotide 2208.

2. The plant promoter of claim 1, wherein the promoter comprises the nucleotide sequence set forth in SEQ ID NO:2.

3. The plant promoter of claim 1, wherein the promoter consists of the nucleotide sequence set forth in SEQ ID NO:2.

4. The plant promoter of claim 1, wherein the promoter consists of the nucleotide sequence set forth in SEQ ID NO:10.

5. The plant promoter of claim 1, wherein the promoter consists of nucleotides 2208-2456 set forth in SEQ ID NO:10 and from 1-2207 contiguous nucleotides set forth in SEQ ID NO:10 that are 5' to and contiguous with nucleotide 2208.

6. A nucleic acid molecule encoding broad-spectrum disease resistance to bacterial blight; wherein said nucleic acid molecule comprises the plant promoter of claim 1 operably linked to a nucleotide sequence encoding a Xa10 promoter comprising the amino acid sequence set forth in SEQ ID NO:14; wherein the causative agent of the bacterial blight is *Xanthomonas oryzae* pv. *Oryzae*.

7. The nucleic acid molecule of claim 6, wherein the nucleotide sequence encoding the Xa10 protein comprises the nucleotide sequence set forth in SEQ ID NO:13.

8. The nucleic acid molecule of claim 6, wherein the nucleotide sequence encoding the Xa10 protein consists of the nucleotide sequence set forth in SEQ ID NO:15.

9. The nucleic acid molecule of claim 6, wherein the nucleotide sequence encoding the Xa10 protein consists of the nucleotide sequence set forth in SEQ ID NO:16.

10. The nucleic acid molecule of claim 6, wherein the nucleotide sequence encoding the Xa10 protein comprises nucleotides 1-381 of the nucleotide sequence set forth in SEQ ID NO:17 and from 1-1834 contiguous nucleotides set forth in SEQ ID NO:17 that are 3' to and contiguous with nucleotide 381.

11. The nucleic acid molecule of claim 6, wherein the nucleotide sequence encoding the Xa10 protein comprises nucleotides 1-759 of the nucleotide sequence set forth in SEQ ID NO:17 and from 1-1456 contiguous nucleotides set forth in SEQ ID NO:17 that are 3' to and contiguous with nucleotide 759.

12. The nucleic acid molecule of claim 7, wherein the nucleotide sequence encoding the Xa10 protein consists of the nucleotide sequence set forth in SEQ ID NO:17.

13. A vector comprising the nucleic acid molecule of claim 6.

14. A transgenic plant cell comprising the nucleic acid molecule of claim 6 stably integrated in its genome.

15. A transgenic plant comprising the nucleic acid molecule of claim 6 stably integrated in its genome.

16. The plant cell or transgenic plant of claim 14 or 15, wherein the plant is rice.

17. The transgenic plant of claim 15, wherein the transgenic plant has broad-spectrum disease resistance to bacterial blight; wherein the causative agent of the bacterial blight is *Xanthomonas oryzae* pv. *Oryzae*.

18. Progeny of the transgenic plant of claim 15, wherein the progeny is produced by selfing said transgenic plant or breeding a second plant with said transgenic plant and recovering the progeny of the selfing or the breeding; wherein the progeny comprise the nucleic acid.

19. A method of preparing a transgenic plant having broad-spectrum resistance to *Xanthomonas oryzae* pv. *Oryzae*—caused bacterial blight; said method comprising introducing the nucleic acid molecule of claim 6 into a plant, wherein the transgenic plant has the nucleic acid molecule stably integrated in its genome.

20. A method of preparing a transgenic plant having broad-spectrum resistance to *Xanthomonas oryzae* pv. *Oryzae*—caused bacterial blight; said method comprising transfecting the nucleic acid molecule of claim 6 into a plant cell or plant cells and regenerating a transgenic plant from the transfected plant cell or transfected plant cells, wherein the transgenic plant has the nucleic acid molecule stably integrated in its genome.

21. The method of claim 19 or 20, wherein the plant is rice.

22. A method of preparing a transgenic plant having broad-spectrum resistance to *Xanthomonas oryzae* pv. *Oryzae*—caused bacterial blight; said method comprising introducing the vector of claim 13 into a plant, wherein the transgenic plant has the nucleic acid molecule stably integrated in its genome.

23. A method of preparing a transgenic plant having broad-spectrum resistance to *Xanthomonas oryzae* pv. *Oryzae*—caused bacterial blight; said method comprising transfecting the vector of claim 13 into a plant cell or plant cells and regenerating a transgenic plant from the transfected plant cell or transfected plant cells, wherein the transgenic plant has the nucleic acid molecule stably integrated in its genome.

* * * * *

SEQUENCE LISTING

```
<160> NUMBER OF SEQ ID NOS: 37

<210> SEQ ID NO 1
<211> LENGTH: 279
<212> TYPE: DNA
<213> ORGANISM: Artificial Sequence
<220> FEATURE:
<223> OTHER INFORMATION: synthetic sequence
```

<400> SEQUENCE: 1
cttattgatg tcgcaatcac ttcaattact tattgatgtc gcaatcacgt tcaccctata 60
taatccccaa atcccctcct cccgatatgc atctccccct actgtacacc accttatata 120
tacacacgtt cactcctata aaaggccctc accaacccat ccttatatat agaagaagag 180
acccatagag agcatcagca cagccgaaac tcgcgagaga tcctcctccc tcctctttca 240
ttcttcgaga tgcagctgat gctcacattc tgcacgggc 279

<210> SEQ ID NO 2
<211> LENGTH: 249
<212> TYPE: DNA
<213> ORGANISM: Artificial Sequence
<220> FEATURE:
<223> OTHER INFORMATION: Synthetic promoter sequence

<400> SEQUENCE: 2
cttattgatg tcgcaatcac ttcaattact tattgatgtc gcaatcacgt tcaccctata 60
taatccccaa atcccctcct cccgatatgc atctccccct actgtacacc accttatata 120
tacacacgtt cactcctata aaaggccctc accaacccat ccttatatat agaagaagag 180
acccatagag agcatcagca cagccgaaac tcgcgagaga tcctcctccc tcctctttca 240
ttcttcgag 249

<210> SEQ ID NO 3
<211> LENGTH: 30
<212> TYPE: DNA
<213> ORGANISM: Oryza sativa
<220> FEATURE:
<221> NAME/KEY: CDS
<222> LOCATION: (1)..(30)

<400> SEQUENCE: 3 atg cag ctg atg ctc aca ttc tgc acg ggc 30
Met Gln Leu Met Leu Thr Phe Cys Thr Gly
1 5 10

<210> SEQ ID NO 4
<211> LENGTH: 10
<212> TYPE: PRT
<213> ORGANISM: Oryza sativa

<400> SEQUENCE: 4

Met Gln Leu Met Leu Thr Phe Cys Thr Gly
1 5 10

<210> SEQ ID NO 5
<211> LENGTH: 23
<212> TYPE: DNA
<213> ORGANISM: Artificial Sequence
<220> FEATURE:
<223> OTHER INFORMATION: TAL effector binding element

<400> SEQUENCE: 5
tataatcccc aaatcccctc ctc 23

<210> SEQ ID NO 6
<211> LENGTH: 25
<212> TYPE: DNA
<213> ORGANISM: Artificial Sequence
<220> FEATURE:
<223> OTHER INFORMATION: TAL effector binding element -continued

<400> SEQUENCE: 6
tgcatctccc cctactgtac accac 25

<210> SEQ ID NO 7
<211> LENGTH: 17
<212> TYPE: DNA
<213> ORGANISM: Artificial Sequence
<220> FEATURE:
<223> OTHER INFORMATION: TAL effector binding element

<400> SEQUENCE: 7
tatatacaca cgttcac 17

<210> SEQ ID NO 8
<211> LENGTH: 24
<212> TYPE: DNA
<213> ORGANISM: Artificial Sequence
<220> FEATURE:
<223> OTHER INFORMATION: TAL effector binding element

<400> SEQUENCE: 8
tataaaaggc cctcaccaac ccat 24

<210> SEQ ID NO 9
<211> LENGTH: 18
<212> TYPE: DNA
<213> ORGANISM: Artificial Sequence
<220> FEATURE:
<223> OTHER INFORMATION: TAL effector binding element

<400> SEQUENCE: 9
tagaagaaga gacccata 18

<210> SEQ ID NO 10
<211> LENGTH: 2456
<212> TYPE: DNA
<213> ORGANISM: Artificial Sequence
<220> FEATURE:
<223> OTHER INFORMATION: synthethic promoter sequence

<400> SEQUENCE: 10
ctaggtttat tggctgagca atgcccaatt ccacaaagac atgctggcgt gctgctgctt 60
gggcagttgg gctatgttga tctacattat atattaaagg taaaaggata aacctttgct 120
cattgataac actcaacatg attagatcta aaagtaaaga tgaagccatg aacacgtttt 180
ttaacagagt aaatccaatc cttcaaaaca caaaagaaaa aaaaaagagc aatgatgaaa 240
cacggtattg ttagagtttg tcttgatgga ccactagact agactcgatg gagcaaacca 300
caatcatcgg ataggcccta caacagaaga actctcatcc actctttacc tcaccgaatc 360
tcctcacgaa attgaaaggt gggaattgag aaacaaacgt tgaaacatat cttgatctga 420
ggcacccagc gtctctcaaa aaaaactaca gattacatca acaaagaatc tttttcttct 480
tccttcctct ctctacctct tcttgagcct aattctttct taccaacaaa aactacgttt 540
tgaccatgat tacccactac tactacatga ttgtgccgca accgcaacca ccaccaccga 600
gcagcaaagc agcagatcgg cgacagttag atcaggcggg ggcctgaact tggcaagaga 660
ggagaagaaa gcaaagagag gggaggagat gagacctcga atcggatgtt cttgaagacg 720
acctcctcga cgttgctgcc gatggtgggt gcggcggtga cggcctcgcc gaggtggagc 780
ttgtagagcg tggtggtctt gccggcgttg tcgagcccca cgacgacgat cttgtactcc 840
ttcgccggga acatcaagaa ccacaccctc gacatccacg cccccatctt cttcctctct 900
gtctcctcct caagcaacca agaaaacacc gaatctgaat ctcgcgccgc ggcggctggc 960
ggctggcggt ggatggatct ccgcgggagg aagtggactg cgagtttggg ggatcggatc 1020
ggcgatgggg gtggaggagg aagaacaaga ggaggtcgga tttggaggag gaaaggtgag 1080
aagggaattg ggtgtggat attcgtgcga agctttcctc tctcatggcc agccgagggg 1140
gatttgggct gggcctcctg tgggctttgg gctgtggaag tagagacatg gcgagtgagc 1200
cggaataagt ctactaatct tccctcgttt ttacgtagag tttaatcgac atccctaaac 1260
cgcaatacca ggaatcttca cctttcatct ttgcaaaacc gtttgactta ggtccgatag 1320
cagtatggat aggtgttttc gctgatgtgg cattctagtt agaaaaaaaa aacatgaggg 1380
ggtccacatg taactgagcc catgtattaa ttgggcccac atgtcagggc tttcttcttc 1440
ctctcctcta ttcccatttc tctccccaat ctccacctat cccctttcc ccagtttata 1500 attgatcata tttatcattt aaactactca atatcgacat taatttgatt gaaaaagaaa 1560
ttagaaaaaa taaaatagaa aaatagaaaa aacggtacgg tcgaaaatag tacctcttaa 1620
acggaaacgg cgtccggtcg attgagaatt tccgtgaccg ttttcagctg ccataggctt 1680
gggccaagcg acaacacttt gggccaagct aaaaacgtct tgggcttttc tgggtcgaaa 1740
gtcgagctaa actcatatgg atccaagtgg ctcacggtgt aaatattagt aggattaatc 1800
ccacatagat agcttacgaa ggttgagagc aatatataaa tccttgcgtc ctaacgacag 1860
tatatgggga aaaaaatttt gtgggggtgt tcgttatata tgcatgaata tatatacata 1920
tatatcttat tatctccccg ggaagcccaa tctctctccc cgggaagccc aatctctctc 1980
aggaatttca agaacttcaa ttgatgaatt tatatttata actaagtcaa ttggtgatcc 2040
tattaccgga acccaaggtc ggttataagt caattggtga tcctattacc ggaaggttaa 2100
gtcaattggt gatcctatta ccggaaggtc caaggtaaag aataaccagt tacacaaggt 2160
ccaaggtaaa gaataaccag ttacaccaaa aggtccaaca ccaaaaactt attgatgtcg 2220
caatcacttc aattacttat tgatgtcgca atcacgttca ccctatataa tccccaaatc 2280
ccctcctccc gatatgcatc tccccctact gtacaccacc ttatatatac acacgttcac 2340
tcctataaaa ggccctcacc aacccatcct tatatataga agaagagacc catagagagc 2400
atcagcacag ccgaaactcg cgagagatcc tcctccctcc tctttcattc ttcgag 2456

<210> SEQ ID NO 11
<211> LENGTH: 4671
<212> TYPE: DNA
<213> ORGANISM: Artificial Sequence
<220> FEATURE:
<223> OTHER INFORMATION: genomic sequence of synthetic gene

<400> SEQUENCE: 11
ctaggtttat tggctgagca atgcccaatt ccacaaagac atgctggcgt gctgctgctt 60
gggcagttgg gctatgttga tctacattat atattaaagg taaaaggata aacctttgct 120
cattgataac actcaacatg attagatcta aaagtaaaga tgaagccatg aacacgtttt 180
ttaacagagt aaatccaatc cttcaaaaca caaaagaaaa aaaaaagagc aatgatgaaa 240
cacggtattg ttagagtttg tcttgatgga ccactagact agactcgatg gagcaaacca 300
caatcatcgg ataggcccta caacagaaga actctcatcc actctttacc tcaccgaatc 360
tcctcacgaa attgaaaggt gggaattgag aaacaaacgt tgaaacatat cttgatctga 420
ggcacccagc gtctctcaaa aaaaactaca gattacatca acaaagaatc tttttcttct 480

-continued

```
tccttcctct ctctacctct tcttgagcct aattctttct taccaacaaa aactacgttt    540
tgaccatgat tacccactac tactacatga ttgtgccgca accgcaacca ccaccaccga    600
gcagcaaagc agcagatcgg cgacagttag atcaggcggg ggcctgaact tggcaagaga    660
ggagaagaaa gcaaagagag gggaggagat gagacctcga atcggatgtt cttgaagacg    720
acctcctcga cgttgctgcc gatggtgggt gcggcggtga cggcctcgcc gaggtggagc    780
ttgtagagcg tggtggtctt gccggcgttg tcgagcccca cgacgacgat cttgtactcc    840
ttcgccggga acatcaagaa ccacaccctc gacatccacg cccccatctt cttcctctct    900
gtctcctcct caagcaacca agaaaacacc gaatctgaat ctcgcgccgc ggcggctggc    960
ggctggcggt ggatggatct ccgcgggagg aagtggactg cgagtttggg ggatcggatc   1020
ggcgatgggg gtggaggagg aagaacaaga ggaggtcgga tttggaggag gaaaggtgag   1080
aagggaattg gggtgtggat attcgtgcga agctttcctc tctcatggcc agccgagggg   1140
gatttgggct gggcctcctg tgggctttgg gctgtggaag tagagacatg gcgagtgagc   1200
cggaataagt ctactaatct tccctcgttt ttacgtagag tttaatcgac atccctaaac   1260
cgcaatacca ggaatcttca cctttcatct ttgcaaaacc gtttgactta ggtccgatag   1320
cagtatggat aggtgttttc gctgatgtgg cattctagtt agaaaaaaaa aacatgaggg   1380
ggtccacatg taactgagcc catgtattaa ttgggcccac atgtcagggc tttcttcttc   1440
ctctcctcta ttcccatttc tctccccaat ctccacctat ccccttttcc ccagtttata   1500
attgatcata tttatcattt aaactactca atatcgacat taatttgatt gaaaaagaaa   1560
ttagaaaaaa taaaatagaa aaatagaaaa aacggtacgg tcgaaaatag tacctcttaa   1620
acggaaacgg cgtccggtcg attgagaatt tccgtgaccg ttttcagctg ccataggctt   1680
gggccaagcg acaacacttt gggccaagct aaaaacgtct tgggcttttc tgggtcgaaa   1740
gtcgagctaa actcatatgg atccaagtgg ctcacggtgt aaatattagt aggattaatc   1800
ccacatagat agcttacgaa ggttgagagc aatatataaa tccttgcgtc ctaacgacag   1860
tatatgggga aaaaaatttt gtgggggtgt tcgttatata tgcatgaata tatatacata   1920
tatatcttat tatctccccg ggaagcccaa tctctctccc cgggaagccc aatctctctc   1980
aggaatttca agaacttcaa ttgatgaatt tatatttata actaagtcaa ttggtgatcc   2040
tattaccgga acccaaggtc ggttataagt caattggtga tcctattacc ggaaggttaa   2100
gtcaattggt gatcctatta ccggaaggtc caaggtaaag aataaccagt tacacaaggt   2160
ccaaggtaaa gaataaccag ttacaccaaa aggtccaaca ccaaaaactt attgatgtcg   2220
caatcacttc aattacttat tgatgtcgca atcacgttca ccctatataa tccccaaatc   2280
ccctcctccc gatatgcatc tccccctact gtacaccacc ttatatatac acacgttcac   2340
tcctataaaa ggccctcacc aacccatcct tatatatatag agaagagacc catagagagc   2400
atcagcacag ccgaaactcg cgagagatcc tcctccctcc tctttcattc ttcgagatgc   2460
agctgatgct cacattctgc acgggccccc tcctgtttgc cgtcctccta ctgatggtat   2520
acctcaagca actcgccgcc gcggcctgcg tcgacgtgct catcatctac ctctgccgct   2580
tcctcctcct ccgcggcatc atcttctccg gcgacggcaa gctacgattc cgcgtcaagg   2640
tagcgatcgg gttcctctac atctccctct cggccatact cttctacctc tctgccgctg   2700
tcatggcgtt gccgccgtgg ggtgcggtgg ccatgtgggg aatggcgctc gtcgccactg   2760
agcttggcta ctccttctta tgcccgtata gctgccgctg cattggtgaa gacgacgagg   2820
agatttcccc cgtctgaggc ccatatatat cacgatggat aaacatatta catactccct   2880
```

-continued

```
ccgtttcaaa atgtttgaca ccattgactt ttcagcacat gtttgaccgt tcgtttcatt   2940

caaaaaaaat tgtgaaatat gtaaaactat atgtgtacat ggaaatatat ttaacaatga   3000

atcaaatgat atgaaaagaa taaataatta cttaaatttt ttgaataaga cgaatggtga   3060

aacacgtact aaaaagtcaa tggtgtcaaa cattttgaaa cggagggagt attaattggt   3120

ttgttagttt gtgttcattc atatatagct gttgtatttt tacggttaat aaagagaaac   3180

cggcgagcgc ctagcagccg gctagtttag tcaaatttgc actatatgta tgttgatact   3240

tgattcatca ttcatatcga tcagggtgtc ctagctagct cgtgtttata tttacgcttg   3300

atgtatgttg atacttgatt tcatcatcca aatttgcact agcttacgtg ttgttccagt   3360

ttgttggggg ccatcgtcaa atcaccctta atttcttgta ccattttggc acgtactaca   3420

catgtatccc tccatccttg tagtttgatt atcacttaag taaaggacgt tgacaccaag   3480

tacaacgaaa cctctatggt tcgaaaatta atttgcatcg atcaaagatg tgttttgtcg   3540

cttcatgtca tacggattgt atcatgcttg ctttaaatat tgcatggagt tacacaaacg   3600

aaaaataatt ttagctgtag ttgtatgcat cactttaatt tagcgaggaa taatatggat   3660

ctgaccacgt actacgcgat tctgctcatc gtcgaggtcg tcttcgcctt cttcttccta   3720

ccgtacagct gcggcagcga cgtcgtggac gagaatatcc cacatgtctg accaggggaa   3780

cgacatcctc tgacgagaga cgtgttcgct gacacgtggg ctccactccc cttaaactca   3840

catgtcagaa attcacgtca cagagcatat actccatcag tcctattata taagggtttt   3900

agatggatga gaagtactac gaatatagat aaaaaatgtc tcgtcgttta tctaaaatct   3960

tttatatttt gggacagagg aaatatatga tcaacttaga tcatttcaaa accaaaacaa   4020

aaactaaaaa gcacggtgaa ctttgtgtgc taccagacca aaatttcctt tggtttgtgt   4080

tagttaatta cctaagtgtg atttcttcat gtcaattagt tagttgatcc atttggtctt   4140

aaactaattt ccacgttcgc aaataaagca gcagcttgct ggctagctag gccttcatgt   4200

tgctcatgta tgcgcacttg tgcagtatga tcaatcaggt caatttaatt atcttattaa   4260

ttatgatgta tatatactcc ctccgtccca aaaaagtgaa tataaaactg aatgtgacat   4320

atgcatatcc agattcattg tcacatccag tattatgttg gttttttata gaacagaggg   4380

agtatgtcac ttcaaattgt tttcaaatct ttaatttatt tcttcttatt tctcgagatc   4440

tacaacggaa gtaacaaata aaacctctaa aaatgatcgt aattctgaaa tttaaaatcg   4500

tattatgtcc aagatctcga tatactagcc agtactcgat ccttatttca taccgtatga   4560

aatccaagga tcagcccagc ccagaccata cagcccaccc cggcccgcgt acggaaacca   4620

acggtctaga atcgctcgac cgaaaaacgc caggtgtcaa ccgcacgagc t            4671
```

<210> SEQ ID NO 12
<211> LENGTH: 3649
<212> TYPE: DNA
<213> ORGANISM: Artificial Sequence
<220> FEATURE:
<223> OTHER INFORMATION: genomic sequence of synthetic gene

<400> SEQUENCE: 12

```
ctaggtttat tggctgagca atgcccaatt ccacaaagac atgctggcgt gctgctgctt     60

gggcagttgg gctatgttga tctacattat atattaaagg taaaaggata aacctttgct    120

cattgataac actcaacatg attagatcta aaagtaaaga tgaagccatg aacacgtttt    180

ttaacagagt aaatccaatc cttcaaaaca caaaagaaaa aaaaaagagc aatgatgaaa    240
```

-continued

```
cacggtattg ttagagtttg tcttgatgga ccactagact agactcgatg gagcaaacca    300
caatcatcgg ataggcccta caacagaaga actctcatcc actctttacc tcaccgaatc    360
tcctcacgaa attgaaaggt gggaattgag aaacaaacgt tgaaacatat cttgatctga    420
ggcacccagc gtctctcaaa aaaaactaca gattacatca acaaagaatc tttttcttct    480
tccttcctct ctctacctct tcttgagcct aattctttct taccaacaaa aactacgttt    540
tgaccatgat tacccactac tactacatga ttgtgccgca accgcaacca ccaccaccga    600
gcagcaaagc agcagatcgg cgacagttag atcaggcggg ggcctgaact tggcaagaga    660
ggagaagaaa gcaaagagag gggaggagat gagacctcga atcggatgtt cttgaagacg    720
acctcctcga cgttgctgcc gatggtgggt gcggcggtga cggcctcgcc gaggtggagc    780
ttgtagagcg tggtggtctt gccggcgttg tcgagcccca cgacgacgat cttgtactcc    840
ttcgccggga acatcaagaa ccacaccctc gacatccacg cccccatctt cttcctctct    900
gtctcctcct caagcaacca agaaaacacc gaatctgaat ctcgcgccgc ggcggctggc    960
ggctggcggt ggatggatct ccgcgggagg aagtggactg cgagtttggg ggatcggatc   1020
ggcgatgggg gtggaggagg aagaacaaga ggaggtcgga tttggaggag gaaaggtgag   1080
aagggaattg gggtgtggat attcgtgcga agctttcctc tctcatggcc agccgagggg   1140
gatttgggct gggcctcctg tgggctttgg gctgtggaag tagagacatg gcgagtgagc   1200
cggaataagt ctactaatct tccctcgttt ttacgtagag tttaatcgac atccctaaac   1260
cgcaatacca ggaatcttca cctttcatct ttgcaaaacc gtttgactta ggtccgatag   1320
cagtatggat aggtgttttc gctgatgtgg cattctagtt agaaaaaaaa aacatgaggg   1380
ggtccacatg taactgagcc catgtattaa ttgggcccac atgtcagggc tttcttcttc   1440
ctctcctcta ttcccatttc tctccccaat ctccacctat ccccttttcc ccagtttata   1500
attgatcata tttatcattt aaactactca atatcgacat taatttgatt gaaaaagaaa   1560
ttagaaaaaa taaaatagaa aaatagaaaa aacggtacgg tcgaaaatag tacctcttaa   1620
acggaaacgg cgtccggtcg attgagaatt tccgtgaccg ttttcagctg ccataggctt   1680
gggccaagcg acaacacttt gggccaagct aaaaacgtct tgggcttttc tgggtcgaaa   1740
gtcgagctaa actcatatgg atccaagtgg ctcacggtgt aaatattagt aggattaatc   1800
ccacatagat agcttacgaa ggttgagagc aatatataaa tccttgcgtc ctaacgacag   1860
tatatgggga aaaaaatttt gtgggggtgt tcgttatata tgcatgaata tatatacata   1920
tatatcttat tatctccccg ggaagcccaa tctctctccc cgggaagccc aatctctctc   1980
aggaatttca agaacttcaa ttgatgaatt tatatttata actaagtcaa ttggtgatcc   2040
tattaccgga acccaaggtc ggttataagt caattggtga tcctattacc ggaaggttaa   2100
gtcaattggt gatcctatta ccggaaggtc caaggtaaag aataaccagt tacacaaggt   2160
ccaaggtaaa gaataaccag ttacaccaaa aggtccaaca ccaaaaactt attgatgtcg   2220
caatcacttc aattacttat tgatgtcgca atcacgttca ccctatataa tccccaaatc   2280
ccctcctccc gatatgcatc tccccctact gtacaccacc ttatatatac acacgttcac   2340
tcctataaaa ggccctcacc aacccatcct tatatataga agaagagacc catagagagc   2400
atcagcacag ccgaaactcg cgagagatcc tcctccctcc tctttcattc ttcgagatgc   2460
agctgatgct cacattctgc acgggccccc tcctgtttgc cgtcctccta ctgatggtat   2520
acctcaagca actcgccgcc gcggcctgcg tcgacgtgct catcatctac ctctgccgct   2580
tcctcctcct ccgcggcatc atcttctccg gcgacggcaa gctacgattc cgcgtcaagg   2640
```

-continued tagcgatcgg gttcctctac atctccctct cggccatact cttctacctc tctgccgctg 2700
tcatggcgtt gccgccgtgg ggtgcggtgg ccatgtgggg aatggcgctc gtcgccactg 2760
agcttggcta ctccttctta tgcccgtata gctgccgctg cattggtgaa gacgacgagg 2820
agatttcccc cgtctgaggc ccatatatat cacgatggat aaacatatta catactccct 2880
ccgtttcaaa atgtttgaca ccattgactt ttcagcacat gtttgaccgt tcgtttcatt 2940
caaaaaaaat tgtgaaatat gtaaaactat atgtgtacat ggaaatatat ttaacaatga 3000
atcaaatgat atgaaaagaa taaataatta cttaaatttt ttgaataaga cgaatggtga 3060
aacacgtact aaaaagtcaa tggtgtcaaa catttgaaa cggagggagt attaattggt 3120
ttgttagttt gtgttcattc atatatagct gttgtatttt tacggttaat aaagagaaac 3180
cggcgagcgc ctagcagccg gctagtttag tcaaatttgc actatatgta tgttgatact 3240
tgattcatca ttcatatcga tcagggtgtc ctagctagct cgtgtttata tttacgcttg 3300
atgtatgttg atacttgatt tcatcatcca aatttgcact agcttacgtg ttgttccagt 3360
ttgttggggg ccatcgtcaa atcaccctta atttcttgta ccattttggc acgtactaca 3420
catgtatccc tccatccttg tagtttgatt atcacttaag taaaggacgt tgacaccaag 3480
tacaacgaaa cctctatggt tcgaaaatta atttgcatcg atcaaagatg tgttttgtcg 3540
cttcatgtca tacggattgt atcatgcttg ctttaaatat tgcatggagt tacacaaacg 3600
aaaaataatt ttagctgtag ttgtatgcat cactttaatt tagcgagga 3649

<210> SEQ ID NO 13
<211> LENGTH: 381
<212> TYPE: DNA
<213> ORGANISM: Oryza sativa
<220> FEATURE:
<221> NAME/KEY: CDS
<222> LOCATION: (1)..(381)

<400> SEQUENCE: 13 atg cag ctg atg ctc aca ttc tgc acg ggc ccc ctc ctg ttt gcc gtc 48
Met Gln Leu Met Leu Thr Phe Cys Thr Gly Pro Leu Leu Phe Ala Val
1 5 10 15 ctc cta ctg atg gta tac ctc aag caa ctc gcc gcc gcg gcc tgc gtc 96
Leu Leu Leu Met Val Tyr Leu Lys Gln Leu Ala Ala Ala Ala Cys Val
20 25 30 gac gtg ctc atc atc tac ctc tgc cgc ttc ctc ctc ctc cgc ggc atc 144
Asp Val Leu Ile Ile Tyr Leu Cys Arg Phe Leu Leu Leu Arg Gly Ile
35 40 45 atc ttc tcc ggc gac ggc aag cta cga ttc cgc gtc aag gta gcg atc 192
Ile Phe Ser Gly Asp Gly Lys Leu Arg Phe Arg Val Lys Val Ala Ile
50 55 60 ggg ttc ctc tac atc tcc ctc tcg gcc ata ctc ttc tac ctc tct gcc 240
Gly Phe Leu Tyr Ile Ser Leu Ser Ala Ile Leu Phe Tyr Leu Ser Ala
65 70 75 80 gct gtc atg gcg ttg ccg ccg tgg ggt gcg gtg gcc atg tgg gga atg 288
Ala Val Met Ala Leu Pro Pro Trp Gly Ala Val Ala Met Trp Gly Met
85 90 95 gcg ctc gtc gcc act gag ctt ggc tac tcc ttc tta tgc ccg tat agc 336
Ala Leu Val Ala Thr Glu Leu Gly Tyr Ser Phe Leu Cys Pro Tyr Ser
100 105 110 tgc cgc tgc att ggt gaa gac gac gag gag att tcc ccc gtc tga 381
Cys Arg Cys Ile Gly Glu Asp Asp Glu Glu Ile Ser Pro Val
115 120 125

-continued

<210> SEQ ID NO 14
<211> LENGTH: 126
<212> TYPE: PRT
<213> ORGANISM: Oryza sativa

<400> SEQUENCE: 14

```
Met Gln Leu Met Leu Thr Phe Cys Thr Gly Pro Leu Leu Phe Ala Val
1               5                   10                  15

Leu Leu Leu Met Val Tyr Leu Lys Gln Leu Ala Ala Ala Ala Cys Val
            20                  25                  30

Asp Val Leu Ile Ile Tyr Leu Cys Arg Phe Leu Leu Leu Arg Gly Ile
        35                  40                  45

Ile Phe Ser Gly Asp Gly Lys Leu Arg Phe Arg Val Lys Val Ala Ile
    50                  55                  60

Gly Phe Leu Tyr Ile Ser Leu Ser Ala Ile Leu Phe Tyr Leu Ser Ala
65                  70                  75                  80

Ala Val Met Ala Leu Pro Pro Trp Gly Ala Val Ala Met Trp Gly Met
                85                  90                  95

Ala Leu Val Ala Thr Glu Leu Gly Tyr Ser Phe Leu Cys Pro Tyr Ser
            100                 105                 110

Cys Arg Cys Ile Gly Glu Asp Asp Glu Glu Ile Ser Pro Val
        115                 120                 125
```

<210> SEQ ID NO 15
<211> LENGTH: 759
<212> TYPE: DNA
<213> ORGANISM: Oryza sativa

<400> SEQUENCE: 15

```
atgcagctga tgctcacatt ctgcacgggc cccctcctgt ttgccgtcct cctactgatg      60

gtatacctca agcaactcgc cgccgcggcc tgcgtcgacg tgctcatcat ctacctctgc     120

cgcttcctcc tcctccgcgg catcatcttc tccggcgacg gcaagctacg attccgcgtc     180

aaggtagcga tcgggttcct ctacatctcc ctctcggcca tactcttcta cctctctgcc     240

gctgtcatgg cgttgccgcc gtggggtgcg gtggccatgt ggggaatggc gctcgtcgcc     300

actgagcttg gctactcctt cttatgcccg tatagctgcc gctgcattgg tgaagacgac     360

gaggagattt cccccgtctg aggcccatat atatcacgat ggataaacat attacatact     420

ccctccgttt caaaatgttt gacaccattg acttttcagc acatgtttga ccgttcgttt     480

cattcaaaaa aaattgtgaa atatgtaaaa ctatatgtgt acatggaaat atatttaaca     540

atgaatcaaa tgatatgaaa agaataaata attacttaaa ttttttgaat aagacgaatg     600

gtgaaacacg tactaaaaag tcaatggtgt caaacatttt gaaacggagg gagtattaat     660

tggtttgtta gtttgtgttc attcatatat agctgttgta tttttacggt taataaagag     720

aaaccggcga gcgcctagca gccggctagt ttagtcaaa                            759
```

<210> SEQ ID NO 16
<211> LENGTH: 1193
<212> TYPE: DNA
<213> ORGANISM: Oryza sativa

<400> SEQUENCE: 16

```
atgcagctga tgctcacatt ctgcacgggc cccctcctgt ttgccgtcct cctactgatg      60

gtatacctca agcaactcgc cgccgcggcc tgcgtcgacg tgctcatcat ctacctctgc     120

cgcttcctcc tcctccgcgg catcatcttc tccggcgacg gcaagctacg attccgcgtc     180
```

```
aaggtagcga tcgggttcct ctacatctcc ctctcggcca tactcttcta cctctctgcc      240

gctgtcatgg cgttgccgcc gtggggtgcg gtggccatgt ggggaatggc gctcgtcgcc      300

actgagcttg gctactcctt cttatgcccg tatagctgcc gctgcattgg tgaagacgac      360

gaggagattt cccccgtctg aggcccatat atatcacgat ggataaacat attacatact      420

ccctccgttt caaaatgttt gacaccattg acttttcagc acatgtttga ccgttcgttt      480

cattcaaaaa aaattgtgaa atatgtaaaa ctatatgtgt acatggaaat atatttaaca      540

atgaatcaaa tgatatgaaa agaataaata attacttaaa ttttttgaat aagacgaatg      600

gtgaaacacg tactaaaaag tcaatggtgt caaacatttt gaaacggagg gagtattaat      660

tggtttgtta gtttgtgttc attcatatat agctgttgta tttttacggt taataaagag      720

aaaccggcga gcgcctagca gccggctagt ttagtcaaat ttgcactata tgtatgttga      780

tacttgattc atcattcata tcgatcaggg tgtcctagct agctcgtgtt tatatttacg      840

cttgatgtat gttgatactt gatttcatca tccaaatttg cactagctta cgtgttgttc      900

cagtttgttg ggggccatcg tcaaatcacc cttaatttct tgtaccattt tggcacgtac      960

tacacatgta tccctccatc cttgtagttt gattatcact taagtaaagg acgttgacac     1020

caagtacaac gaaacctcta tggttcgaaa attaatttgc atcgatcaaa gatgtgtttt     1080

gtcgcttcat gtcatacgga ttgtatcatg cttgctttaa atattgcatg gagttacaca     1140

aacgaaaaat aatttagct gtagttgtat gcatcacttt aatttagcga gga            1193

<210> SEQ ID NO 17
<211> LENGTH: 2215
<212> TYPE: DNA
<213> ORGANISM: Oryza sativa

<400> SEQUENCE: 17

atgcagctga tgctcacatt ctgcacgggc cccctcctgt ttgccgtcct cctactgatg       60

gtatacctca agcaactcgc cgccgcggcc tgcgtcgacg tgctcatcat ctacctctgc      120

cgcttcctcc tcctccgcgg catcatcttc tccggcgacg gcaagctacg attccgcgtc      180

aaggtagcga tcgggttcct ctacatctcc ctctcggcca tactcttcta cctctctgcc      240

gctgtcatgg cgttgccgcc gtggggtgcg gtggccatgt ggggaatggc gctcgtcgcc      300

actgagcttg gctactcctt cttatgcccg tatagctgcc gctgcattgg tgaagacgac      360

gaggagattt cccccgtctg aggcccatat atatcacgat ggataaacat attacatact      420

ccctccgttt caaaatgttt gacaccattg acttttcagc acatgtttga ccgttcgttt      480

cattcaaaaa aaattgtgaa atatgtaaaa ctatatgtgt acatggaaat atatttaaca      540

atgaatcaaa tgatatgaaa agaataaata attacttaaa ttttttgaat aagacgaatg      600

gtgaaacacg tactaaaaag tcaatggtgt caaacatttt gaaacggagg gagtattaat      660

tggtttgtta gtttgtgttc attcatatat agctgttgta tttttacggt taataaagag      720

aaaccggcga gcgcctagca gccggctagt ttagtcaaat ttgcactata tgtatgttga      780

tacttgattc atcattcata tcgatcaggg tgtcctagct agctcgtgtt tatatttacg      840

cttgatgtat gttgatactt gatttcatca tccaaatttg cactagctta cgtgttgttc      900

cagtttgttg ggggccatcg tcaaatcacc cttaatttct tgtaccattt tggcacgtac      960

tacacatgta tccctccatc cttgtagttt gattatcact taagtaaagg acgttgacac     1020

caagtacaac gaaacctcta tggttcgaaa attaatttgc atcgatcaaa gatgtgtttt     1080

gtcgcttcat gtcatacgga ttgtatcatg cttgctttaa atattgcatg gagttacaca     1140
```

-continued aacgaaaaat aattttagct gtagttgtat gcatcacttt aatttagcga ggaataatat 1200
ggatctgacc acgtactacg cgattctgct catcgtcgag gtcgtcttcg ccttcttctt 1260
cctaccgtac agctgcggca gcgacgtcgt ggacgagaat atcccacatg tctgaccagg 1320
ggaacgacat cctctgacga gagacgtgtt cgctgacacg tgggctccac tccccttaaa 1380
ctcacatgtc agaaattcac gtcacagagc atatactcca tcagtcctat tatataaggg 1440
ttttagatgg atgagaagta ctacgaatat agataaaaaa tgtctcgtcg tttatctaaa 1500
atcttttata ttttgggaca gaggaaatat atgatcaact tagatcattt caaaaccaaa 1560
acaaaaacta aaaagcacgg tgaactttgt gtgctaccag accaaaattt cctttggttt 1620
gtgttagtta attacctaag tgtgatttct tcatgtcaat tagttagttg atccatttgg 1680
tcttaaacta atttccacgt tcgcaaataa agcagcagct tgctggctag ctaggccttc 1740
atgttgctca tgtatgcgca cttgtgcagt atgatcaatc aggtcaattt aattatctta 1800
ttaattatga tgtatatata ctccctccgt cccaaaaaag tgaatataaa actgaatgtg 1860
acatatgcat atccagattc attgtcacat ccagtattat gttggttttt tatagaacag 1920
agggagtatg tcacttcaaa ttgttttcaa atctttaatt tatttcttct tatttctcga 1980
gatctacaac ggaagtaaca aataaaacct ctaaaaatga tcgtaattct gaaatttaaa 2040
atcgtattat gtccaagatc tcgatatact agccagtact cgatccttat ttcataccgt 2100
atgaaatcca aggatcagcc cagcccagac catacagccc accccggccc gcgtacggaa 2160
accaacggtc tagaatcgct cgaccgaaaa acgccaggtg tcaaccgcac gagct 2215

<210> SEQ ID NO 18
<211> LENGTH: 21
<212> TYPE: DNA
<213> ORGANISM: Artificial Sequence
<220> FEATURE:
<223> OTHER INFORMATION: primer sequence

<400> SEQUENCE: 18
aaaaagcctg aactcaccgc g 21

<210> SEQ ID NO 19
<211> LENGTH: 21
<212> TYPE: DNA
<213> ORGANISM: Artificial Sequence
<220> FEATURE:
<223> OTHER INFORMATION: primer sequence

<400> SEQUENCE: 19
tacttctaca cagccatcgg t 21

<210> SEQ ID NO 20
<211> LENGTH: 21
<212> TYPE: DNA
<213> ORGANISM: Artificial Sequence
<220> FEATURE:
<223> OTHER INFORMATION: primer sequence

<400> SEQUENCE: 20
cacgggcccc ctcctgtttg c 21

<210> SEQ ID NO 21
<211> LENGTH: 23
<212> TYPE: DNA
<213> ORGANISM: Artificial Sequence
<220> FEATURE:

-continued

<223> OTHER INFORMATION: primer sequence

<400> SEQUENCE: 21
cctcgtcgtc ttcaccaatg cag 23

<210> SEQ ID NO 22
<211> LENGTH: 23
<212> TYPE: DNA
<213> ORGANISM: Artificial Sequence
<220> FEATURE:
<223> OTHER INFORMATION: primer sequence

<400> SEQUENCE: 22
ctaggtttat tggctgagca atg 23

<210> SEQ ID NO 23
<211> LENGTH: 22
<212> TYPE: DNA
<213> ORGANISM: Artificial Sequence
<220> FEATURE:
<223> OTHER INFORMATION: primer sequence

<400> SEQUENCE: 23
tctaactgtc gccgatctgc tg 22

<210> SEQ ID NO 24
<211> LENGTH: 23
<212> TYPE: DNA
<213> ORGANISM: Artificial Sequence
<220> FEATURE:
<223> OTHER INFORMATION: primer sequence

<400> SEQUENCE: 24
ttcttcttcc ttcctctctc tac 23

<210> SEQ ID NO 25
<211> LENGTH: 22
<212> TYPE: DNA
<213> ORGANISM: Artificial Sequence
<220> FEATURE:
<223> OTHER INFORMATION: primer sequence

<400> SEQUENCE: 25
tcactcgcca tgtctctact tc 22

<210> SEQ ID NO 26
<211> LENGTH: 22
<212> TYPE: DNA
<213> ORGANISM: Artificial Sequence
<220> FEATURE:
<223> OTHER INFORMATION: primer sequence

<400> SEQUENCE: 26
aggaaaggtg agaagggaat tg 22

<210> SEQ ID NO 27
<211> LENGTH: 23
<212> TYPE: DNA
<213> ORGANISM: Artificial Sequence
<220> FEATURE:
<223> OTHER INFORMATION: primer sequence

<400> SEQUENCE: 27
gtttagctcg actttcgacc cag 23

<210> SEQ ID NO 28
<211> LENGTH: 23
<212> TYPE: DNA
<213> ORGANISM: Artificial Sequence
<220> FEATURE:
<223> OTHER INFORMATION: primer sequence

<400> SEQUENCE: 28
ctgggtcgaa agtcgagcta aac 23

<210> SEQ ID NO 29
<211> LENGTH: 28
<212> TYPE: DNA
<213> ORGANISM: Artificial Sequence
<220> FEATURE:
<223> OTHER INFORMATION: primer sequence

<400> SEQUENCE: 29
ccatcgtgat atatatgggc ctcagacg 28

<210> SEQ ID NO 30
<211> LENGTH: 22
<212> TYPE: DNA
<213> ORGANISM: Artificial Sequence
<220> FEATURE:
<223> OTHER INFORMATION: primer sequence

<400> SEQUENCE: 30
gccatactct tctacctctc tg 22

<210> SEQ ID NO 31
<211> LENGTH: 25
<212> TYPE: DNA
<213> ORGANISM: Artificial Sequence
<220> FEATURE:
<223> OTHER INFORMATION: primer sequence

<400> SEQUENCE: 31
ttattctttt catatcattt gattc 25

<210> SEQ ID NO 32
<211> LENGTH: 22
<212> TYPE: DNA
<213> ORGANISM: Artificial Sequence
<220> FEATURE:
<223> OTHER INFORMATION: primer sequence

<400> SEQUENCE: 32
gtaaaactat atgtgtacat gg 22

<210> SEQ ID NO 33
<211> LENGTH: 22
<212> TYPE: DNA
<213> ORGANISM: Artificial Sequence
<220> FEATURE:
<223> OTHER INFORMATION: primer sequence

<400> SEQUENCE: 33
tcctcgctaa attaaagtga tg 22

<210> SEQ ID NO 34
<211> LENGTH: 19
<212> TYPE: DNA
<213> ORGANISM: Artificial Sequence
<220> FEATURE:
<223> OTHER INFORMATION: primer sequence -continued

```
<400> SEQUENCE: 34

ggcatcatct tctccggcg                                              19


<210> SEQ ID NO 35
<211> LENGTH: 19
<212> TYPE: DNA
<213> ORGANISM: Artificial Sequence
<220> FEATURE:
<223> OTHER INFORMATION: primer sequence

<400> SEQUENCE: 35

gcagctatac gggcataag                                              19


<210> SEQ ID NO 36
<211> LENGTH: 20
<212> TYPE: DNA
<213> ORGANISM: Artificial Sequence
<220> FEATURE:
<223> OTHER INFORMATION: primer sequence

<400> SEQUENCE: 36

ccagtaagtc ctcagccatg                                             20


<210> SEQ ID NO 37
<211> LENGTH: 21
<212> TYPE: DNA
<213> ORGANISM: Artificial Sequence
<220> FEATURE:
<223> OTHER INFORMATION: primer sequence

<400> SEQUENCE: 37

tttcagacac catcaaacca g                                           21
```

UNITED STATES PATENT AND TRADEMARK OFFICE
CERTIFICATE OF CORRECTION

PATENT NO. : 9,528,120 B2
APPLICATION NO. : 14/439968
DATED : December 27, 2016
INVENTOR(S) : Zhongchao Yin et al.

Page 1 of 1

It is certified that error appears in the above-identified patent and that said Letters Patent is hereby corrected as shown below:

In the Claims

Column 47, Line 67 "promoter" should be -- protein --

Signed and Sealed this
Eighteenth Day of April, 2017

Michelle K. Lee
*Director of the United States Patent and Trademark Office*